United States Patent
Goldstein et al.

(10) Patent No.: US 9,682,031 B2
(45) Date of Patent: Jun. 20, 2017

(54) MICROCAPSULES COMPRISING BENZOYL PEROXIDE AND TOPICAL COMPOSITIONS COMPRISING THEM

(75) Inventors: Danny Goldstein, Kibbutz Dafna (IL); Tal Sade, MaAlot (IL); Yuri Yasman, Carmiel (IL); Olga Privalova, Kibbutz LeHavot HaBashan (IL); Lior Benaltabet, Kibbutz Dafna (IL)

(73) Assignee: Tagra Biotechnologies Ltd., Natania (IL)

( * ) Notice: Subject to any disclaimer, the term of this patent is extended or adjusted under 35 U.S.C. 154(b) by 597 days.

(21) Appl. No.: 13/500,423

(22) PCT Filed: Oct. 7, 2010

(86) PCT No.: PCT/IL2010/000813
§ 371 (c)(1),
(2), (4) Date: Jun. 25, 2012

(87) PCT Pub. No.: WO2011/042902
PCT Pub. Date: Apr. 14, 2011

(65) Prior Publication Data
US 2012/0258177 A1    Oct. 11, 2012

Related U.S. Application Data

(60) Provisional application No. 61/249,397, filed on Oct. 7, 2009.

(51) Int. Cl.
| | | |
|---|---|---|
| A61K 8/11 | (2006.01) | |
| A61K 8/81 | (2006.01) | |
| A61K 49/18 | (2006.01) | |
| A61K 8/73 | (2006.01) | |
| A61K 8/38 | (2006.01) | |
| A61K 9/00 | (2006.01) | |
| A61K 9/50 | (2006.01) | |
| A61K 31/327 | (2006.01) | |
| A61K 31/7056 | (2006.01) | |
| A61K 45/06 | (2006.01) | |
| A61K 9/06 | (2006.01) | |

(52) U.S. Cl.
CPC .......... *A61K 8/731* (2013.01); *A61K 8/11* (2013.01); *A61K 8/38* (2013.01); *A61K 8/8152* (2013.01); *A61K 9/0014* (2013.01); *A61K 9/5015* (2013.01); *A61K 9/5026* (2013.01); *A61K 9/5047* (2013.01); *A61K 31/327* (2013.01); *A61K 31/7056* (2013.01); *A61K 45/06* (2013.01); *A61K 9/06* (2013.01); *A61K 2800/412* (2013.01)

(58) Field of Classification Search
None
See application file for complete search history.

(56) References Cited

U.S. PATENT DOCUMENTS

| | | | |
|---|---|---|---|
| 4,056,611 A | 11/1977 | Young | |
| 4,401,835 A | 8/1983 | Tarasov | |
| 5,879,716 A | 3/1999 | Katz et al. | |
| 6,491,953 B1 | 12/2002 | Sojka et al. | |
| 6,932,984 B1 | 8/2005 | Babtsov et al. | |
| 2002/0064541 A1 | 5/2002 | Lapidot et al. | |
| 2009/0191245 A1* | 7/2009 | Fredon et al. | 424/401 |

FOREIGN PATENT DOCUMENTS

| | | |
|---|---|---|
| CN | 1367714 | 9/2002 |
| CN | 101309746 | 11/2008 |
| FR | 2833841 A1 | 12/2001 |
| FR | 2833841 | 6/2003 |
| WO | WO 01/19509 | 3/2001 |
| WO | 2007002349 A2 | 1/2007 |
| WO | 2007023495 A2 | 3/2007 |
| WO | 2007132134 A2 | 11/2007 |
| WO | WO 2007/132134 | 11/2007 |
| WO | 2009138978 A2 | 11/2009 |
| WO | WO 2009/138978 | 11/2009 |
| WO | WO 2011/042902 | 4/2011 |

OTHER PUBLICATIONS

International Preliminary Report on Patentability Dated Apr. 19, 2012 From the International Bureau of WIPO Re. Application No. PCT/IL2010/000813.
International Search Report and the Written Opinion Dated Oct. 18, 2011 From the International Searching Authority Re. Application No. PCT/IL2010/000813.
Office Action Dated Feb. 28, 2013 From the State Intellectual Property Office of the People's Republic of China Re. Application No. 201080055390.2 and Its Translation Into English.
Hines et al. "A Combination Acne Regimen Using Encapsulated Benzoyl Peroxide, Salicyclic Acid, and a Botanical Blend for Treatment of Teenage Patients", Journal of the Academy of Dermatology, XP025963956, 60(3): AB21, # P735, Mar. 1, 2009.
Hines et al, "A Combination Acne Regimen Using Encapsulated Benzoyl Peroxide, Salicylic Acid, and a Botanical Blend for Treatment of Teenage Patients", Journal of the American Academy of Dermatology, vol. 60, No. 3, p. AB21 (2009).
Jelvehgari et al, "The Microsponge Delivery System of Benzoyl Peroxide: Preparation, Characterization and Release Studies", International Journal of Pharmaceutics, No. 308, pp. 124-132 (2006).
Fakhouri et al., "Advancement in Benzoyl Peroxide-Based Acne Treatment: Methods to Increase Both Efficacy and Tolerability", Journal for drugs and Dermatology, vol. 8(7), pp. 657-661 (2009).
Office Action Dated Aug. 7, 2014 From the State Intellectual Property Office of the People's Republic of China Re. Application No. 201080055390.2 and Its Translation Into English.
Office Action Dated Dec. 19, 2013 From the State Intellectual Property Office of the People's Republic of China Re. Application No. 201080055390.2 and Its Translation Into English.

(Continued)

*Primary Examiner* — Misook Yu
*Assistant Examiner* — Kauser Akhoon

(57) ABSTRACT

The present invention provides microcapsules comprising benzoyl peroxide and topical compositions comprising them, optionally along with other active ingredients, particularly for the treatment of acne.

28 Claims, 22 Drawing Sheets

(56) References Cited

OTHER PUBLICATIONS

Official Action Dated Jan. 9, 2014 From the US Patent and Trademark Office Re. U.S. Appl. No. 13/500,423.
Search Report Dated Dec. 19, 2013 From the State Intellectual Property Office of the People's Republic of China Re. Application No. 201080055390.2 and Its Translation Into English.
Office Action Dated Apr. 18, 2014 From the State Intellectual Property Office of the People's Republic of China Re. Application No. 201080055390.2 and Its Translation Into English.
Liao et al. "Practical Manual of Novel Techniques, Novel Process and Novel Formulation for Cosmetic Production and of International General Managemendards", p. 504, Apr. 2004.
Yu et al. "Microcapsules and Microcapsulation Techniques", Modem Plastic Processing and Applications, 12(6): 55-59, Dec. 31, 2000. & English Translation.
Examination Report Dated Mar. 2, 2017 From the Servico Publico Federal, Ministerio da Industria, Comercio Exterior e Servicos, Instituto Nacional da Propriedade Industrial do Brasil Re. Application No. 112012007798-8 and Its Translation Into English. (13 pages).

\* cited by examiner

MICROCAPSULES COMPRISING BENZOYL PEROXIDE AND TOPICAL COMPOSITIONS COMPRISING THEM

FIELD OF THE INVENTION

The present invention relates to microcapsules comprising benzoyl peroxide and to topical compositions comprising said microencapsulated benzoyl peroxide, particularly for the treatment of acne, optionally along with other active ingredients.

BACKGROUND OF THE INVENTION

Acne vulgaris is a common skin condition, most common during adolescence. It is characterized by noninflammatory follicular papules or comedones and by inflammatory papules, pustules, and nodules in its more severe forms. The areas more affected by acne are the face, the upper part of the chest, and the back. Acne lesions are commonly referred to as pimples, blemishes, spots, zits, or simply acne. In severe acne conditions, the naturally occurring bacteria *Propionibacterium acnes* can cause inflammation, leading to inflammatory lesions (papules, infected pustules, or nodules) in the dermis around the microcomedo or comedone, which results in redness and may result in scarring or hyperpigmentation.

Since acne affects virtually every adolescent at some point in time, the choice of therapy should be principally based on the type of lesion and the severity of the acne, but psychosocial disability relating to the disease and the presence of scarring may also influence the approach to treatment. A combination of treatments can greatly reduce the amount and severity of acne in many cases.

Benzoyl peroxide $(C_6H_5CO)_2O_2$, is a colorless, odorless, tasteless, crystalline solid that is stable at ordinary room temperatures but which is flammable and is capable of exploding when confined and subjected to grinding, heat or flame. It is a powerful oxidizing agent but is non-toxic to man and causes no local injurious effects and has been employed as an effective antibacterial and keratolytic agent in the treatment of acne.

Gels, creams, lotions and ointments containing the bactericide benzoyl peroxide in concentrations of 2.5%-5% and 10% are used for treatment of mild to moderate acne. In addition to its therapeutic effect as a keratolytic, benzoyl peroxide also prevents new lesions by killing *P. acnes* without generating bacterial resistance like antibiotics. However, benzoyl peroxide routinely causes dryness, local irritation and redness and can cause excessive skin irritation. Its poor water solubility, coupled with its chemical instability in other solvents, presents challenges with respect to formulating topical products with optimal bioavailability, stability, and tolerability. In addition, with some commercially available products in which benzoyl peroxide comprises crystals in suspension, aggregation of benzoyl peroxide can occur on the skin surface in large clumps, resulting in poor penetration into sebaceous follicles.

Many attempts have been made to provide an efficient delivery system for BPO. U.S. Pat. No. 4,056,611 discloses a therapeutic composition for the treatment of acne consisting of a stable dispersion of finely divided particles of benzoyl peroxide in an aqueous alcohol vehicle. U.S. Pat. No. 4,401,835 discloses a method for the preparation of benzoyl peroxide in crystalline form, which crystals may range in size below 10 microns, and its incorporation into cosmetic and pharmaceutical preparations. U.S. Pat. No. 6,491,953 discloses a controlled release composition comprising an adsorbent polymer, an active agent which may be benzoyl peroxide, and a release retardant, wherein the composition has an improved ability to release the active agent over an extended time period.

Methods to increase both efficacy and tolerability of benzoyl peroxide-based acne treatment have been recently reviewed (Fakhouri T, Yentzer B A, Feldman S R. Advancement in benzoyl peroxide-based acne treatment: methods to increase both efficacy and tolerability. J Drugs Dermatol. 8(7):657-61, 2009). Novel vehicles including a microparticle delivery system have been discussed in this review citing, for example, Jelvehgari et al. (2006) which disclose a microsponge delivery system of benzoyl peroxide consisting of ethyl cellulose microparticles prepared using an emulsion solvent diffusion method by adding an organic internal phase containing benzoyl peroxide, ethyl cellulose and dichloromethane into a stirred aqueous phase containing polyvinyl alcohol. The micrograph of the microsponges showed that they were spherical in shape, contained pores and had a mean particle size within a range of 230-450 μm (Jelvehgari M, Siahi-Shadbad M R, Azarmi S, Martin G P, Nokhodchi A. The microsponge delivery system of benzoyl peroxide: preparation, characterization and release studies. Int J Pharm. 308(1-2):124-32, 2006).

It would be highly desirable to provide benzoyl peroxide formulations that are stable, permit immediate release of the benzoyl peroxide to the skin and present reduced irritancy while keeping effectiveness in the treatment of acne.

U.S. Pat. No. 6,932,984 and WO 2007/023495 of the same applicant of the present application disclose a method for microencapsulation of substances by the solvent removal method using non-chlorinated solvents. The method is based on physical processes only which do not cause any change of original physical and/or chemical properties, biological activity, and safety of raw materials during the process. This method affords physical stability of the microcapsules during the preparation of the formulation, high ability to entrap the active agents, protection of the active agents inside the microcapsules, prevention of the diffusion of the microencapsulated active agents to the external water phase in a water-based preparation, and optimal controlled release only upon application to the skin.

SUMMARY OF THE INVENTION

It has now been found by the present inventors that by using the solvent removal method with non-chlorinated solvents, microcapsules containing benzoyl peroxide can be obtained that combine optimal protection/isolation of the benzoyl peroxide with its optimal release upon contact with the skin.

The present invention thus relates to stable microcapsules for topical application comprising 0.1-99% benzoyl peroxide and a shell of a wall-forming polymeric material selected from a polyacrylate, a polymethacrylate, a cellulose ether, a cellulose ester or a combination thereof.

The invention further relates to methods of preparing said microcapsules and to water-based compositions for topical application comprising them, particularly for treatment of acne.

The invention further relates to microcapsules containing a green pigment and to compositions for topical application comprising said microcapsules.

DETAILED DESCRIPTION OF THE INVENTION

Figure 1A:
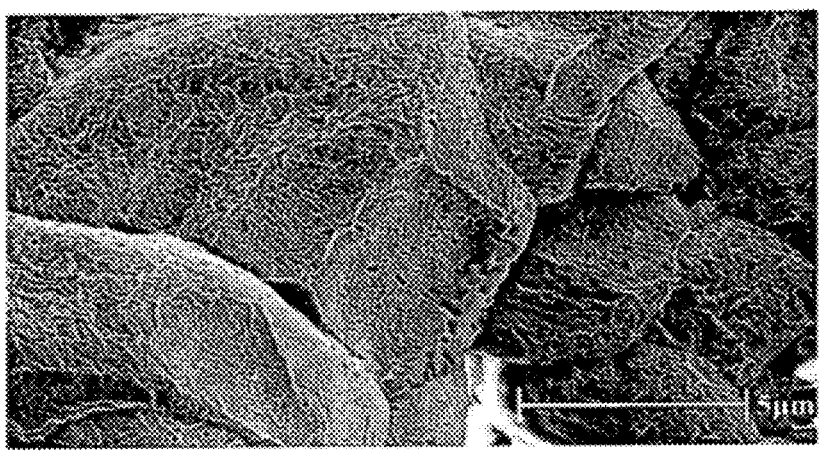
FIGS. 1A-1E show scanning electron microscope (SEM) images of free BPO in magnifications ×16000 (1A), ×8000 (1B), ×4000 (1C), ×1000 (1D), and ×125 (1E).
Figure 1B:
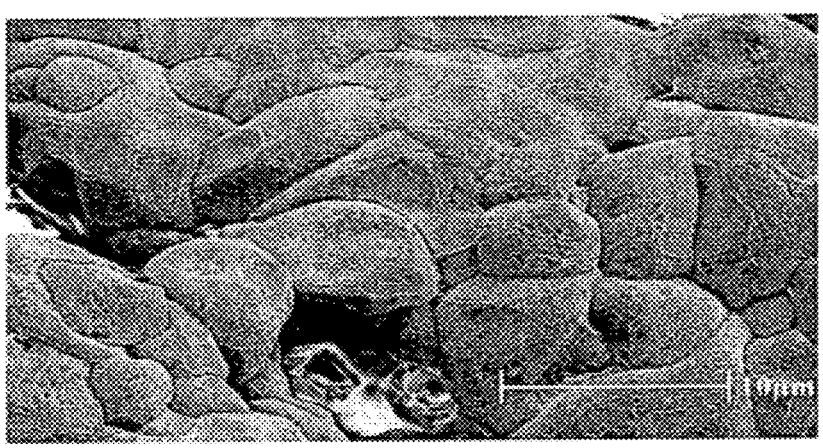
Figure 1C:
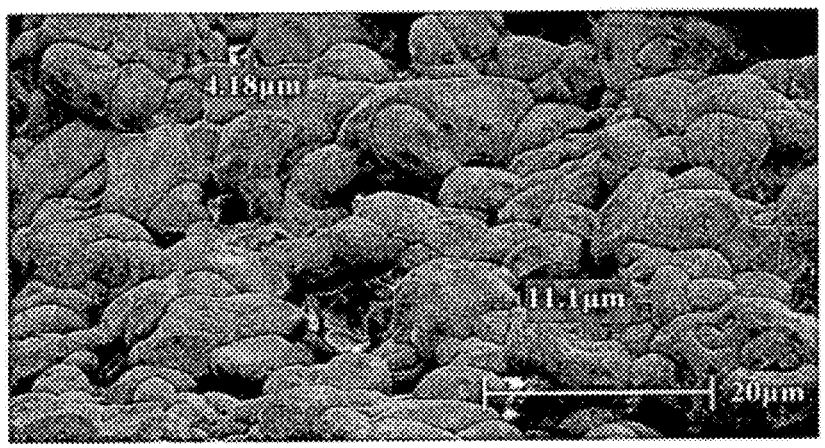
Figure 1D:
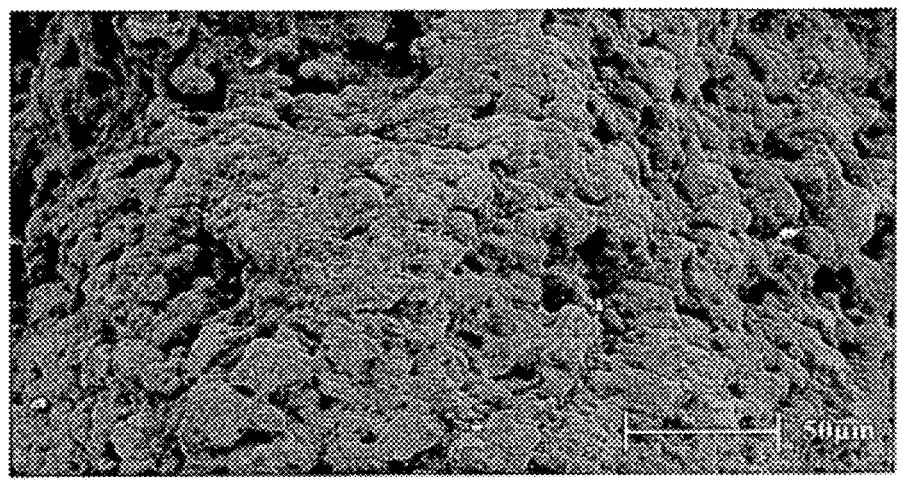
Figure 1E:
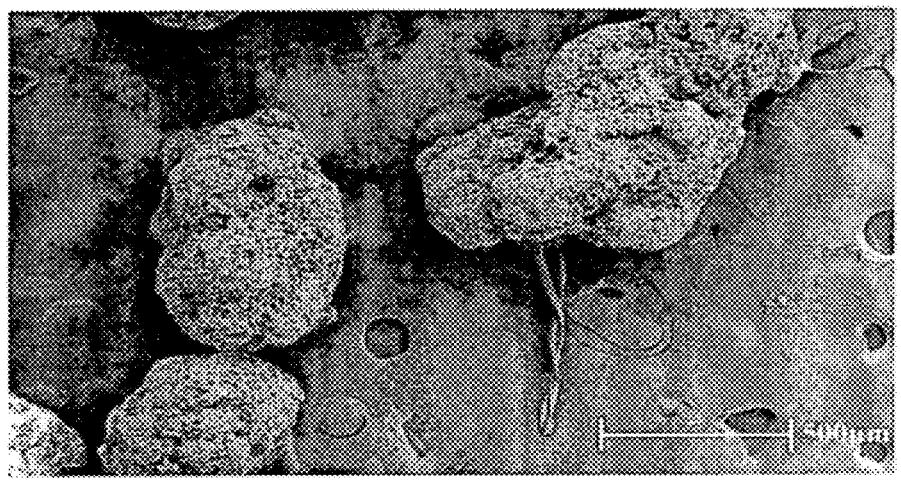

In one aspect the present invention relates to stable microcapsules for topical application comprising 0.1-99% benzoyl peroxide and a shell of a wall-forming polymeric material selected from a polyacrylate, a polymethacrylate, a cellulose ether, a cellulose ester, or a combination thereof.

The term "microcapsule", as used herein, refers to a spherical microparticle consisting of a polymeric shell serving as a wall-forming material and encapsulated benzoyl peroxide located within the core of the microcapsule and partially also found in the shell matrix, but not on the outer surface of the shell. Microcapsules are distinct from microspheres, which consist of spherical homogeneous granules of the active substance dispersed in a polymer and are, in strict sense, spherically empty particles.

The term "wall-forming polymer" refers to a polymer or a combination of two or more different polymers as defined herein, which form a component of the external wall or layer or shell of the microcapsules. The term "polymer shell" refers to a polymer layer containing the wall-forming polymer(s) and, optionally, further components such as a plasticizer.

The term "stable" as used herein refers to the stability of the benzoyl peroxide within the microcapsule, i.e. the encapsulation protects the benzoyl peroxide and prevents its release/diffusion from the microcapsules in a water-based preparation The method used for the preparation of the microcapsules of the invention as described hereinafter is based on the microencapsulation solvent removal method disclosed by the applicant of the present application in the above-mentioned U.S. Pat. No. 6,932,984 and WO 2007/023495. According to this technology, the active ingredient is found in the core of the microcapsule. This technique seals each micro-capped ingredient from chemical and cross-link reactions, degradation, color change or loss of potency during production and for extended periods in storage and the active ingredient is "released on demand", namely, by rubbing on the skin.

In accordance with the present invention, contrary to the active ingredients disclosed in U.S. Pat. No. 6,932,984 and WO 2007/02349, the benzoyl peroxide is found not only within the microcapsule core but part of it is solubilized in the polymer shell. However, no benzoyl peroxide is found on the outer surface of the shell. The microcapsules prevent the release/diffusion of the benzoyl peroxide out of the microcapsules in a water-based preparation for use on the skin. In addition, following contact with the skin, the benzoyl peroxide is released from the microcapsules not only by rubbing on the skin, as disclosed in U.S. Pat. No. 6,932,984 and WO 2007/02349 for other active ingredients, but also by diffusion or by a combination of both.

The microcapsules of the invention have a mean particle size within a range from about 1 to about 500 μm. In certain embodiments, the mean particle size is under 130, preferably under 100 μm, and may be within the ranges of 10 to 130 μm, 10 to 100 μm, 20 to 90 μm, 30 to 70 μm, or 40 to 60 μm. In preferred embodiments, the mean particle size of the microcapsules is from 30 to 70 μm, for example, 30, 40, 50, 60 or 70 μm.

The wall-forming polymeric material may be a polyacrylate, a polymethacrylate, a cellulose ether or ester, or a combination thereof. In some preferred embodiments, the polymer is a polymethacrylate, more preferably poly(methyl methacrylate) co-methacrylic acid (PMMA) or ammonio methacrylate copolymer type B (also known as Eudragit RSPO®). In other preferred embodiments, the polymer is a cellulose ether or ester such as, but not limited to, methyl cellulose, ethyl cellulose, hydroxypropyl methyl cellulose, hydroxypropyl cellulose, cellulose acetate, cellulose acetate phthalate, hydroxypropyl methyl cellulose acetate phthalate. In other preferred embodiments, the wall-forming polymeric material is a combination of the mentioned polymers such as, but not limited to, combinations of ammonio methacrylate copolymer type B (Eudragit RSPO®) with either PMMA or ethyl cellulose (EC).

The microcapsules of the invention may further comprise one or more additives selected from one or more plasticizers, a wax, boron nitride, or a combination thereof. In one embodiment the additive is one or more plasticizers selected from tricaprylin (TC), trilaurin (TL), acetyl tributyl citrate (ATBC), acetyl triethyl citrate (ATEC), triethyl citrate (TEC), $C_{12}$-$C_{15}$ alkyl benzoate (AB), isopropyl myristate, monoglycerol oleate, tripalmitin, triacetin, or paraffin oil. In another embodiment the additive is a wax selected from beeswax, abil wax, lanolin, triisostearin, isostearyl isostearate, stearic acid, cetyl alcohol, palmitic acid, glyceryl stearate, or propylene glycol mono palmitostearate (PGMP). In yet another embodiment the additive is a fatty acid. In still another embodiment the additive is boron nitride (BN).

In some embodiments of the invention, the microcapsules have no additives. For example, as shown hereinafter in Example 3, Table 4 (samples 1-4, 7) and in Example 11, Table 7 (samples 65, 75, 77, 91 and 92), microcapsules were prepared containing benzoyl peroxide and a shell of PMMA, ethyl cellulose or a combination of PMMA/Eudragit RSPO® without any additive.

In other embodiments, the microcapsules of the invention contain one or more plasticizers. For example, as shown hereinafter in Example 3, Table 4 (samples 5-6, 8-12, 15-16, 22-23), microcapsules were prepared containing benzoyl peroxide and (i) a shell of ethyl cellulose further comprising as plasticizer triethyl citrate (TEC), trilaurin (TL), acetyl triethyl citrate (ATEC), acetyl tributyl citrate (ATBC), or a mixture of TL/ABTC or ATBC/alkyl benzoate (AB); (ii) a shell of EC/Eudragit RSPO® and as plasticizer ATEC or ATBC; or (iii) a shell of PMMA/Eudragit RSPO® and as plasticizer tricaprylin (TC) or acetyl triethyl citrate (ATEC). Such microcapsules may contain a further additive that is beneficial such as boron nitride (BN) along with the plasticizer, e.g., trilaurin (see samples 13-14 in Table 4).

In yet other embodiments, the microcapsules of the invention contain a wax as an additive. For example, as shown hereinafter in Example 11, Table 7 (sample 95) microcapsules were prepared containing benzoyl peroxide and a shell of ethyl cellulose further comprising propylene glycol mono palmitostearate (PGMP) as a wax.

In some further embodiments, the microcapsules of the invention contain as additives both a plasticizer and a wax. For example, as shown hereinafter in Example 3, Table 4 (samples 17-21), microcapsules were prepared containing benzoyl peroxide, a shell of ethyl cellulose and further comprising as additives a plasticizer/wax combination trilaurin/beeswax, trilaurin/lanolin, trilaurin/triisostearin, trilaurin/isostearyl isostearate, trilaurin/abil wax. Other combinations of plasticizers/wax can be used and are encompassed by the invention such as, but not limited to, trilaurin/stearic acid, trilaurin/cetyl alcohol, trilaurin/palmitic acid, and trilaurin/glyceryl stearate.

The amount of benzoyl peroxide in the microcapsules of the invention is within a range from 20-99%, 40-95%, or preferably 60-90%. The amount weight/weight of the polymers from the total microcapsule weight varies according to the polymer and the presence of additives.

In another aspect, the present invention relates to a method for preparation of the microcapsules of the invention, the method comprising:

a) preparing an organic solution of benzoyl peroxide with the wall-forming polymeric material in ethyl acetate, optionally in the presence of one or more additives;

b) mixing said organic solution with an aqueous solution containing an emulsifier, under stirring, to form an emulsion;

c) adding to the emulsion formed in (b) an excess amount of water containing the same emulsifier as in (b) to initiate extraction of the organic solvent from the emulsion, thus obtaining microcapsules;

d) optionally allowing sedimentation of the microcapsules; and e) isolating said microcapsules of c) or d) by filtration, subsequently washing with water or with 10% alcohol, and optionally drying the wet capsules.

In one embodiment the additive is a plasticizer such as, but not limited to, tricaprylin (TC), trilaurin (TL), acetyl tributyl citrate (ATBC), acetyl triethyl citrate (ATEC), triethyl citrate (TEC), $C_{12}$-$C_{15}$ alkyl benzoate (AB), isopropyl myristate, monoglycerol oleate, tripalmitin, triacetin, paraffin oil, or a combination thereof. In another embodiment the additive is a wax such as, but not limited to, beeswax, abil wax, lanolin, triisostearin, isostearyl isostearate, stearic acid, cetyl alcohol, palmitic acid, glyceryl stearate, propylene glycol mono palmitostearate (PGMP), or a combination thereof. In yet another embodiment the additive is a fatty acid. In still another embodiment the additive is boron nitride (BN).

The preferred emulsifier used in step (b) and (c) is polyvinyl alcohol. If the microcapsules are left for sedimentation (step (d)), the time is within the range of 8-48 hours, preferably 12-16 hours.

As mentioned above, the method of the invention is based on the solvent removal method and uses non-chlorinated solvent. In the emulsion prepared in step (b), the droplet size is within the range from about 40 to 200 μm. During the extraction of the organic solvent from the droplets, the polymer hardens and forms a thin solid wall enveloping the benzoyl peroxide and any present additives. The separation of the soft microcapsules is carried out by suspension and filtration followed by washing, thus obtaining a wet bulk batch of microcapsules. The drying process of the microcapsules is performed under controlled conditions with adequate equipment resulting in a free-flowing powder. In certain embodiments the drying step is avoided and the microcapsules are kept as slurry/paste form with 20% of water. The solvent removal method has advantages in that it permits (i) physicochemical stability of bioactive components in extreme conditions, (ii) release on demand of bioactive components on the skin; (iii) homogeneous texture of formulation; and (iv) high loading of the active component (up to 99% of benzoyl peroxide).

The microcapsules of the invention are advantageous in affording the protection of a sensitive ingredient such as benzoyl peroxide from the detrimental effects of the environment such as oxidation or hydrolysis. The polymeric shell of the microcapsules is hermetic and prevents benzoyl peroxide from diffusing out of the microcapsule in an aqueous environment, even if a small amount of water from the external phase permeates within the microcapsules. In other words, it allows incorporation of such microencapsulated benzoyl peroxide into water-based, e.g., oil-in-water (o/w) creams or topical aqueous gels, without affecting the stability of the active ingredient.

Contrary to other encapsulation methods such as liposomes, nanoparticles, matrix, sponge, cyclodextrins and silica, the microcapsules of the invention provide good isolation of the active agents, high loading capacity, physical stability, homogeneity in formulation, protection of the active agents under extreme conditions and the ability to trigger release profile on the skin. None of the encapsulation methods available today can simultaneously provide physical stability of the microcapsules during the preparation of the formulation, high ability to entrap the active agents, protection of the active agents inside the microcapsules and optimal controlled release upon application to the skin.

As shown in Examples 1-3, benzoyl peroxide (BPO) was successfully/efficiently encapsulated by the solvent removal method of the invention. The method is based on physical processes only and does not cause any change of original physical and/or chemical properties, biological activity, and stability of raw materials during the process. The yield of production of the microcapsules of the invention was 80% and above.

Figure 7:
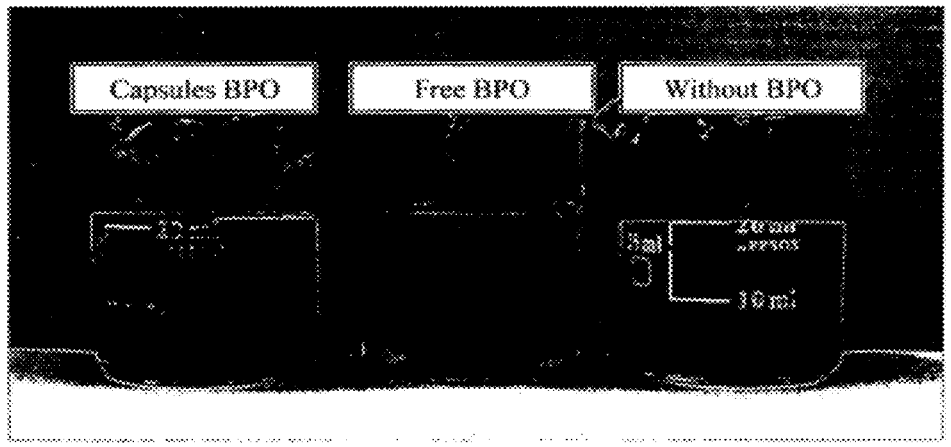
FIG. 7 depicts the results of a qualitative diffusion study using the congo red solution test: right beaker—congo red solution without addition of benzoyl peroxide (BPO); middle beaker—change of color of congo red to yellow due to oxidation by free BPO; left beaker—no change of color of congo red solution in the presence of BPO microcapsules of the invention.
Figure 8:
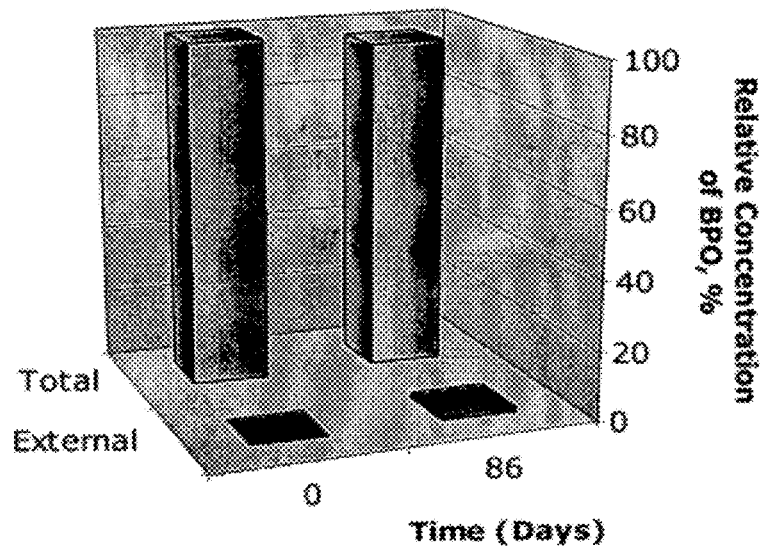
FIG. 8 shows BPO concentration in total gel preparation before and after incubation at 40° C. as compared to the concentration in the external water phase only. Microcapsules were incorporated in gel preparation and incubated over 86 days at 40° C. No significant diffusion was observed from microcapsules to the external medium of the formulation.
Figure 21:
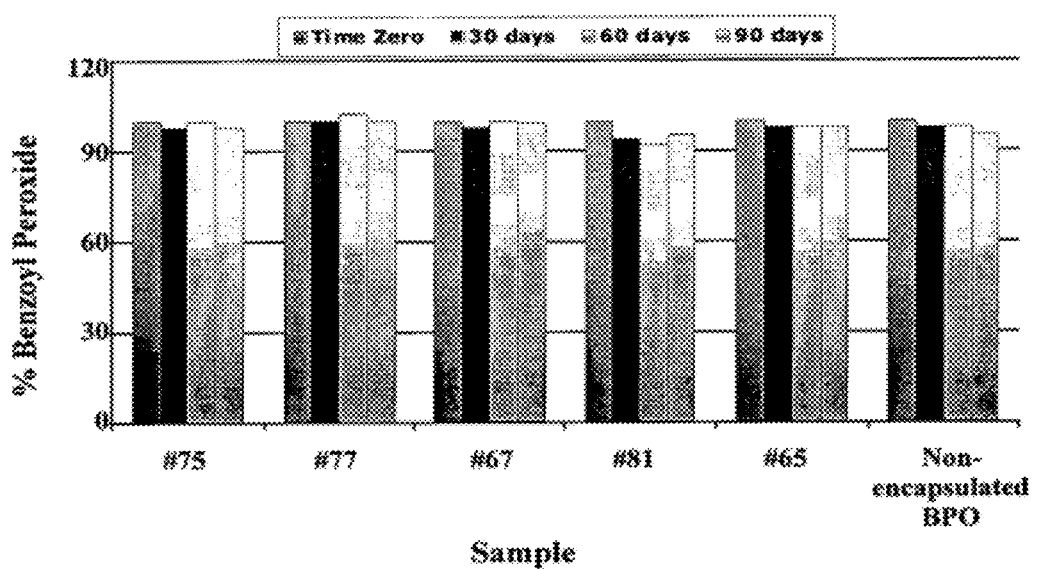
FIG. 21 shows the stability of BPO in aqueous gel formulations comprising BPO microcapsules (samples #65, #67, #75, #77 and #81). After 90 days of incubation at 40° C. there is a negligible decrease in the concentration of BPO in the microcapsules and also in the non-encapsulated BPO.

It is shown herein (Examples 5 and 6) that the BPO microcapsules of the invention incorporated in model formulations prevented undesirable chemical reactions under stress test conditions. The microcapsules demonstrated protective effect both qualitatively (Example 5) and quantitatively (Example 6). FIG. 7 demonstrates that BPO microcapsules prevented congo red from reacting with BPO and therefore protected BPO from oxidation. Further, under stress stability test (after 86 days of incubation at 40° C.) there is a negligible decrease in the concentration of BPO in the microcapsules (FIG. 8 and FIG. 21).

It is further demonstrated herein (Example 13) that higher loads of BPO in the microcapsules (higher than 80%) result in increased stability of clindamycin phosphate in the composition.

Scanning electron microscopy (SEM) results show that the microcapsules are of spherical shape having a polymeric shell with either a smooth surface (FIGS. 2A-2C) or a rough aerated surface (non-smooth superficial surface) (FIGS. 3A-3C, 4A-4C, 5A-5B, 11A-11B, 12A-12B, 13A-13B, 14A-14B, 15A-15B, 16A-16B, 17A-17B, 18A-18C, 19A-19B and 20a-20B). FIGS. 3A, 13A, 17A, 18A and 20A, which contain cross sections of BPO microcapsules, demonstrate that the spherical void cavities of various diameters in the shell, do not span the whole width of the shell and are not conventional pores since they are not open from both sides like channels. Thus, despite the rough perforated surface, the shell is not porous and does not allow leakage of the encapsulated BPO.

The improved BPO compositions have a small particle size compared with those prepared by conventional grinding techniques and the time and potential hazards associated with grinding are avoided. The small particle size of the BPO flocculants result in increased surface area of the active ingredient on the skin for a given concentration of BPO.

Figure 6A:
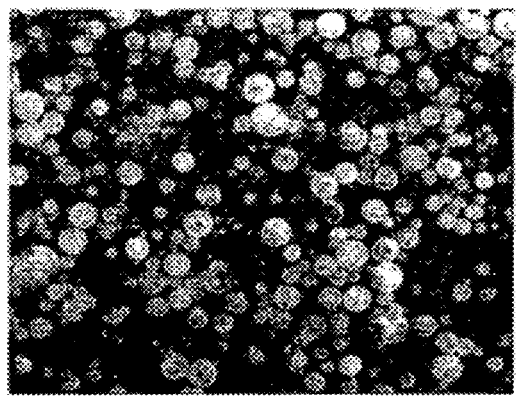
FIGS. 6A-6B show light microscope images of BPO microcapsules in gel, before (6A) and after (6B) application of a gentle pressure.
Figure 6B:
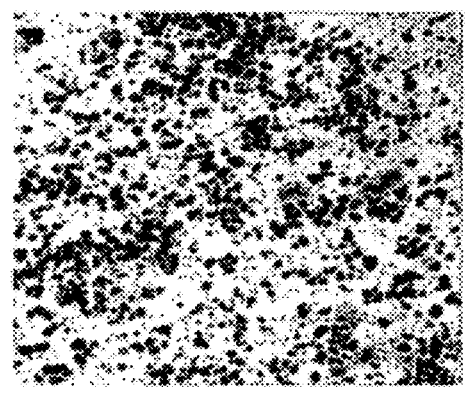

As shown in FIGS. 6A-6B, the microcapsules are breakable only upon application of mild pressure and releasing of BPO from the microcapsules is observed upon rubbing. Softening of the microcapsules was observed at good level.

As shown in Example 14, the BPO microcapsules of the invention, do not cause irritation following a single exposure for 48 hours. In addition, the wall forming polymers comprised in said microcapsules, did not induce a contact dermal irritation in the tenth application in the Draize repeated insult patch test (RIPT), as shown in Example 15. Non-irritating compositions containing microencapsulated BPO are useful in preparing products suitable for use in contact with the skin for the topical treatment of acne or other dermatological disorders.

The microcapsules of the invention exhibit a marked potential in the design of aqueous based topical formulations comprising active ingredients sensitive to oxidation or hydrolysis. In addition, the prolonged stability and controlled release possibilities afforded by the microcapsules of the invention allow for the delivery of biologically active ingredients onto the skin long after the production at the manufacturing facility.

In yet another aspect, the present invention relates to a composition for topical application comprising the microcapsules of the invention.

In one embodiment, the final concentration of benzoyl peroxide in the composition is in the range of 0.1-10%, more preferably 1-5% (w/w)

The composition of the invention may be in any form suitable for topical application such as, but not limited to, a gel, cream, ointment, paste or lotion intended for skin care. In some preferred embodiments, the composition is in the form of a water-based gel. Benzoyl peroxide is lipophilic and yet development of an aqueous-based gel formulation is attractive due to irritation caused when applying current alcohol-based formulations. A cream formulation may be either water-based or oil-based formulation.

The compositions of the invention are prepared by methods well-known in the art. When a gel is prepared, gelling agents are used such as natural gums, e.g., xanthan gum.

The compositions of the invention comprising the benzoyl peroxide microcapsules are particularly useful for the treatment of acne. Indeed, the efficacy of the microcapsules was confirmed in a clinical study, in which the severity of acne was reduced from grade 2 to grade 0 within 4 weeks, in patients treated with a gel formulation comprising the benzoyl peroxide microcapsules of the invention (data not presented).

Since benzoyl peroxide is in many cases considered more efficacious if used in a combination therapy for acne, the present invention also encompasses compositions further comprising one or more active agents selected from antibiotics and vitamin A or a derivative thereof.

In one embodiment, the composition comprises an antibiotic such as clarithromycin, erythromycin, clindamycin or azithromycin, preferably clindamycin that is used in several commercial preparations with benzoyl peroxide for the treatment of acne. In Example 13, gel preparations comprising the BPO microcapsules of the invention and clindamycin phosphate were prepared and examined for stability. It is known that BPO in a composition together with clindamycin causes decomposition of clindamycin. Surprisingly it was found, that increasing the loading of BPO in BPO microcapsules, results in increased stability of clindamycin in gel formulations comprising both encapsulated BPO and clindamycin phosphate, following 90 days incubation at 40° C. (FIG. 22B).

The vitamin A for use in combination with the benzoyl peroxide may be Retinol (the animal form of vitamin A) and the vitamin A derivative may be Retinal (aldehyde form), Retinoic acid (acid form), e.g. tretinoin (all-trans retinoic acid) or a retinyl ester, e.g., retinol palmitate. In preferred embodiments, the vitamin A is Retinol.

Figure 9:
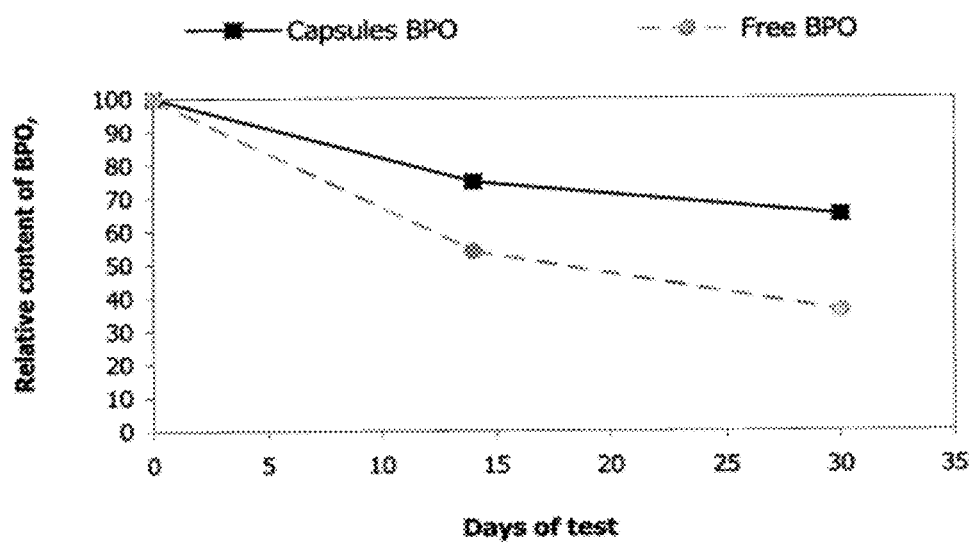
FIG. 9 shows stability of BPO microcapsules vs. free BPO (5% final BPO concentration) in gel containing 1% free retinol, incubated over 30 days at 40° C.

It was found that combining BPO with vitamin A or vitamin A derivatives in the same composition, causes degradation of both BPO and vitamin A. However, as shown in FIG. 9, when the BPO is encapsulated in the microcapsules of the invention, the degradation is much lower than for free BPO.

The antibiotic and the vitamin A or derivative thereof may be each microencapsulated in separate microcapsules or they may be present in the composition in a free form.

One of the problems in the treatment of acne is that therapeutic active ingredients may alleviate the inflammatory lesions of acne but do not effect the external clinical signs such as erythema, telangiectasia or redness. These external clinical signs have impact on patients' social and professional life, and particularly disturb adolescents under treatment.

In order to overcome or minimize these external clinical signs, the present invention provides pharmaceutical compositions comprising a therapeutic agent for treatment of acne and further comprising a dye for simultaneous treatment of the acne pathology and the clinical signs associated therewith. In some preferred embodiments, both the therapeutic agent and the dye are separately microencapsulated in a physically and chemically stable composition thus controlling any possible undesired interactions between the encapsulated agents, and maintaining the bioavailability of the active agents.

The dye for neutralizing the diffuse redness on the face of acne patients should have an opposite color to red on the chromatic circle and thus should be green. Any suitable dye/pigment of green color can be used in accordance with the invention. In preferred embodiments, the green dye is a green pigment such as chromium oxide green, preferably microencapsulated in microcapsules of mean size of about 70 μm. Upon application on the skin, the shell fractures and the pigment is immediately released thus causing simultaneous masking of skin redness and giving the patient the feeling of immediate effect by concealing the lesions.

Thus, in accordance with the present invention, microcapsules for topical application are used comprising a green dye in a shell of a wall-forming polymeric material selected from a polyacrylate, polymethacrylate, cellulose ether or ester, or a combination thereof. In certain embodiments, the green dye is the chromium oxide green pigment, and the wall-forming polymeric material is a combination of ethyl cellulose and Eudragit RSPO®. These microcapsules comprise also a wax, preferably tribehenin, and may comprise also a white pigment, preferably $TiO_2$, and further additives such as boron nitride.

In a further embodiment, the present invention relates to a composition for topical use for treatment of acne comprising benzoyl peroxide as the therapeutic agent, more particularly the microencapsulated benzoyl peroxide of the present invention, and chromium oxide green as the dye, preferably microencapsulated as described herein. This composition may further comprise other active agents such as an antibiotic and/or Vitamin A or a derivative thereof as described hereinabove.

The microencapsulation of the chromium oxide green is carried according to the solvent removal method described in the above-referenced U.S. Pat. No. 6,932,984 and WO 2007/02349. However, the pigment has to undergo a pretreatment before the actual microencapsulation. The pretreatment consists in blending the pigment with a wax, preferably tribehenin. The wax is heated until receiving a melt, the pigment is added gradually under heating (80-100° C.) to receive a homogeneous dispersion, the hot-melt is poured on an aluminum foil, left to cool to room temperature, broken to slices and then grinded to a powder. The pigment powder is then microencapsulated in a shell of one or more suitable wall-forming polymers as defined herein, preferably a combination of Eudragit RSPO® and ethyl cellulose. Additives can be added to the microcapsules such as boron nitride (for softening) and $TiO_2$ (white pigment).

In accordance with the present invention, the method for the preparation of chromium oxide green pigment microcapsules comprises:

a) heating a wax, preferably tribehenin, until receiving a melt, adding the pigment to the wax melt under heating (80-100° C.) to receive a homogeneous dispersion, cooling, breaking the solid formed and grinding to a powder;

b) preparing an organic solution of the pigment powder of a) with a wall-forming polymeric material selected from a polyacrylate, polymethacrylate, cellulose ether or ester, or a combination thereof in ethyl acetate, optionally in the presence of one or more additives;

c) mixing said organic solution with an aqueous solution containing an emulsifier, under stirring, to form an emulsion;

d) adding to the formed emulsion an excess amount of water containing the same emulsifier of (c) to initiate extraction of the organic solvent from the emulsion, thus obtaining microcapsules;

e) optionally leaving for a time sufficient to allow sedimentation of the microcapsules; and f) isolating said microcapsules of d) or e) by filtration, subsequently washing with water or with 10% alcohol, and drying the wet capsules.

In certain embodiments, the wall-forming material is a combination of ammonio methacrylate copolymer type B and ethyl cellulose and the additives are $TiO_2$ and BN.

The compositions of the invention may comprise further ingredients used in topical applications, e.g. components for skin soothing.

The specific combination of benzoyl peroxide along with antibiotics and/or vitamin A or derivative thereof enables optimal therapeutic efficiency through the simultaneous activation of different mechanisms for the treatment of acne, namely, reducing the surplus secretion of oily matter from the sebaceous glands, clearance of dead skin cells which block the pores, and treatment of bacteria in the blocked hair follicles. The specific composition together with microencapsulation technology enables optimal treatment for acne. In particular, the composition provides a therapeutically effective amount of the active agent at the site of the lesion upon usage (improving availability), reduced systemic absorbance and improved safety profile.

The composition of the invention comprising encapsulated BPO affords many advantages including: high loading capacity (up to 99%, relative to up to 20% in available encapsulation methods); high physical stability of the microcapsules during the process of preparation; protection of BPO in the microcapsules, thus obtaining shelf-life which is 20 to 30 times that of the non-encapsulated BPO; homogeneity of the microcapsules in size and shape which enables uniform and constant release of the BPO upon application on the skin; homogeneous dispersion of the microcapsules in the composition which guarantees uniform concentration of the BPO in the composition; optimal controlled release only upon rubbing on the skin and direct biological activity on the lesion (the polymeric shell is on the one hand hard and impermeable, and on the other hand soft enough to enable the release of the BPO upon application on the skin); combination of several active agents in the composition while avoiding unwanted interactions between them; and biocompatibility (water-based, non-oily formulations which avoid side effects such as irritations, redness and stinging which characterize available solutions).

The compositions of the invention are aqueous based formulations comprising the highly effective topical antibacterial agent benzoyl peroxide alone or in combination with vitamin A or its derivative, protected from environment degradation by a special microcapsule coating. These compositions are advantageous, providing the discretion and the lack of brightness (which is elicited by the alcoholic and fatty preparations) on the one hand, while enhancing the efficiency of the novel microencapsulated products, on the other hand.

The microencapsulation enables two or three encapsulated active pharmaceuticals ingredients to be combined in a single, stable formulation. Drug combinations can provide improved efficacy that lead to better clinical results and patient compliance. Antimicrobial therapy for acne has been complicated by the emergence of antibiotic-resistant strains of P. acnes. Increasing P. acnes resistance can be overcome by judicious use of retinoids in combination with novel efficient antibiotics to reduce inflammation and infection. Thus, these new encapsulated active pharmaceutical ingredients will provide the dermatologist with a new topical safe arsenal of innovative products able to efficiently treat mild to moderately severe acne lesions that have been refractory to available products.

It is demonstrated herein (Example 8, particularly FIG. 8 and Example 13 particularly FIGS. 21 and 22A-22B) that this improved technology can increase the shelf life of active ingredients and formulations while ensuring the safety and enabling appropriate cosmetic efficacy. In addition, it was shown that owing to the special wall characteristics of these novel microcapsules, the active ingredients can be retained within the microcapsules in an aqueous based product and the ingredient release is achieved by a physical pressure applied on the topical product upon administration to the skin (FIGS. 6A-6B). All the capsules maintain their original shape in the topical composition. The active ingredient is fully protected by the capsule wall, thus preventing contact with other ingredients within the composition, especially water. Only when the microcapsules are subjected to a pressing action, most of the active ingredient is released onto the target area.

The green pigments are encapsulated using the method of encapsulation as described herein above, resulting in white powder of microcapsules. Incorporation of these microcapsules which contain green pigment into the anti-acne formulation (emulsion, cream, gel, etc.) does not change the basic color of formulation. Only upon application, an appearance of green color is achieved resulting from capsules' rupture. The green pigment serves to mask the redness which results from the inflammation process and give the patient the feeling of immediate effect.

The invention will now be illustrated by the following non-limiting Examples.

EXAMPLES

Materials

The following materials used in the examples are listed with their abbreviations used herein and their suppliers: benzoyl peroxide (BPO 75%; Aldrich); ethyl cellulose (EC; ASHA Cellulose PVT, Ltd., India); triethylcitrate (TEC), acetyl triethyl citrate (ATEC) and acetyl tributyl citrate (ATBC) from Unitex Chemical Corporation, Greensboro, N.C.; polyvinyl alcohol (PVA 4%; Kuraray, Japan); Aerosil 200 colloidal silica (Wacker Chemie AG, Germany); poly (methyl methacrylate) co-methacrylic acid (PMMA; average MW ca. 15,000; Sigma-Aldrich); ammonio methacrylate copolymer Type B (EuRSPO; Eudragit RSPO®, Rohm); tricaprylin (TC, Abitex Corp.); trilaurin (TL; Stearinerie Dubois Fils, France); Beeswax (PEG-7 Dimethicone Beeswax, Beeswax siliconized water-dispersible 6423 WD Siliconized Beeswax) and synthetic lanoline (bis-diglyceryl-polyacyladipate-2), both from Kahl, Poland; $C_{12}$-$C_{15}$ alkyl benzoate (AB; Polygon Chemical Ltd.); boron nitride (BN, Mizushima Ferroalloy Co Ltd, Japan); triisostearin (Pelemol GTIS of Phoenix Chemicals Inc.); isostearyl isostearate (A&E Connock); Abil wax (Cetyl dimethicone Abil wax 9814, Goldschmidt Chemical Corp.); Geogard (Lonza, Switzerland); Xanthan gum (Roeper GmbH, Germany); propylene glycol mono palmitostearate (Gattfoss'e, Toronto, Canada); chromium oxide green (Sun Chemical); Syncro-wax HRC (Tribehenin, Croda, UK); titanium dioxide—X402 (Kemira).

Example 1. General Procedure for Preparation of Benzoyl Peroxide Microcapsules

The microcapsules are prepared by the solvent removal method comprising:

a) preparing an organic solution of the benzoyl peroxide with the wall-forming polymeric material in ethyl acetate, optionally with one or more additives such as plasticizers, waxes, or a mixture thereof;

b) mixing said organic solution with an aqueous solution containing an emulsifier, under stirring, to form an emulsion;

c) adding to the formed emulsion an excess amount of water containing the same emulsifier of (b) to initiate extraction of the organic solvent from the emulsion, thus obtaining microcapsules;

d) optionally leaving for a time sufficient to allow sedimentation of the microcapsules; and e) isolating said microcapsules by filtration, subsequently washing with water or with 10% alcohol (to remove ethyl acetate residues) and optionally drying the wet capsules.

Example 2. Preparation of Ethyl Cellulose Microcapsules Containing Benzoyl Peroxide 2.1 Preparation of Organic Phase ("Master Batch"):

An organic phase (herein called "master batch" (MB)) was prepared by gradually adding 33 g of the wall-forming polymer ethyl cellulose N7 (33 g), under stirring, into 400 g of ethyl acetate, and stirring well until the mixture was homogeneous (about 15 min). The plasticizer triethylcitrate (1 g) was added to this mixture and it was further stirred for about 3 min. BPO (benzoyl peroxide 75%, 88 g, which equals to 66 g 100% BPO) was then gradually added to the mixture and stirring was continued until a transparent solution was obtained (composition detailed in Table 1).

TABLE 1

MB (organic phase) composition

| Material | Loading for 100 g dry product (%) | Loading component of MB (g) |
|---|---|---|
| Ethyl cellulose N7 | 33 | 33 |
| Triethyl citrate | 1 | 1 |
| Benzoyl Peroxide 75%, | 88 | 88 |
| Ethyl Acetate | — | 400 |

2.2 Preparation of the Emulsion:

A water solution was prepared by mixing water (1055 g) with polyvinyl alcohol (PVA 4%, 70 g) such that the water phase consisted of 0.25% PVA. Ethyl acetate (125 g) was added to the water phase under stirring at 400 RPM for 10 min. The master batch of 2.1 above was gradually added into the ethyl acetate/water emulsion under stirring at 800 RPM, and further stirred for additional 10 min (composition detailed in Table 2).

TABLE 2

Emulsion composition

| Material | Loading for 100 g portion (g) |
|---|---|
| Water | 1055 |
| PVA solution 4% (0.25% from water phase) | 70 |
| Ethyl Acetate (10% from total emulsion weight) | 125 |
| MB | 522 |

2.3 Procedure of Extraction:

An extraction phase was prepared by mixing 13150 g water with 165 g PVA solution 4% (composition detailed in table 3). The emulsion of 2.2 above was gradually added into the extraction phase under stirring at 600 RPM and was further stirred for additional 15 min. The extraction mixture was then left for overnight sedimentation of the formed microcapsules.

TABLE 3

Extraction content

| Material | Loading for 100 g portion (g) |
|---|---|
| PVA solution 4% | 165 |
| Water | 13150 |
| Emulsion | 1772 |

2.4 Washing and Drying Procedure:

The sedimented microcapsules of 2.3 above were separated by filtration as a "cake". Water (0.6 L) was added to the filtrated "cake" and mixed for 15 min followed by filtration. The "cake" of microcapsules was then put into a container, crumbled and dried at room temperature for 48 hours. The dry capsules were mixed with Aerosil 200 colloidal silica (0.5% from total weight) and sifted with an automatic sifter. The sifted microcapsules containing benzoyl peroxide were kept at room temperature.

The mean particle size of the BPO microcapsules obtained was 50 μm, BPO content (measured by HPLC) was 65%, and the yield of production was 82%.

Example 3. Preparation of Additional BPO Microcapsules

Various types of microcapsules comprising BPO were prepared using the procedure detailed above in Examples 1 and 2. The composition, mean particle size and BPO content of the different microcapsules are detailed in Table 4 below.

The wall-forming polymer was poly(methyl methacrylate) co-methacrylic acid (PMMA) alone (samples 1-3) or in combination with ammonio methacrylate copolymer Type B (Eudragit RSPO®) (samples 4-6), ethyl cellulose (EC N7 or N45) alone (samples 7-14 and 17-23), or in combination with Eudragit RSPO® (samples 15-16). In samples 1-4 and 7 no plasticizer was used. In the other samples the following plasticizers were used: acetyl triethyl citrate (ATEC), tricaprylin (TC), triethyl citrate (TEC), trilaurin (TL), acetyl tributyl citrate (ATBC) or $C_{12}$-$C_{15}$ alkyl benzoate (AB), alone or in combination. In samples 17-21 the following waxes were used in combination with the plasticizer trilaurin: beeswax, lanolin, triisostearin, isostearyl isostearate, and abil wax. In samples 13 and 14, boron nitride was used in combination with the plasticizer trilaurin.

TABLE 4

BPO microcapsules prototypes

| | | | | | | Capsules | |
|---|---|---|---|---|---|---|---|
| | | Loading raw materials, % | | | Yield, | Mean particle | BPO HPLC, |
| N | Samples | Polymer | | Plasticizer/Wax | BPO | % | size, μm | % |
| 1 | 1 | PMMA | 55 | — | 0 | 45 | 87 | 70 | 45 |
| 2 | 2* | PMMA | 34 | — | 0 | 66 | 85 | 50 | 64 |

TABLE 4-continued

BPO microcapsules prototypes

| N | Samples | Polymer | Loading raw materials, % | | | Yield, % | Capsules | |
| | | | Plasticizer/Wax | | BPO | | Mean particle size, μm | BPO HPLC, % |
|---|---|---|---|---|---|---|---|---|
| 3 | 3 | PMMA | 12 | — | 0 | 88 | 78 | 40 | 88 |
| 4 | 9 | PMMA/EuRSPO | 40/10 | — | 0 | 50 | 84 | 30 | 51 |
| 5 | 12 | PMMA/EuRSPO | 35/10 | ATEC | 10 | 50 | 87 | 40 | 52 |
| 6 | 14 | PMMA/EuRSPO | 36/9 | TC | 10 | 50 | 90 | 45 | 50 |
| 7 | 4* | EC-7 | 34 | — | 0 | 66 | 77 | 70 | 66 |
| 8 | 10* | EC | 33 | TEC | 1 | 66 | 82 | 50 | 65 |
| 9 | 16* | EC | 29 | TL/ATBC | 18/1 | 52 | 90 | 50 | 42 |
| 10 | 18 | EC | 29 | ATBC/AB | 18/1 | 52 | 80 | agglomerates | 51 |
| 11 | 21* | EC | 15 | TL | 30 | 55 | 88 | 40 | 55 |
| 12 | 20 | EC | 10 | TL | 37 | 53 | 86 | 30 | 54 |
| 13 | 23 | EC | 10 | TL/BN | 10/30 | 50 | 91 | 130 | 49 |
| 14 | 24 | EC | 2 | TL/BN | 18/30 | 50 | 85 | 400 | 50 |
| 15 | 29 | EC/EuRSPO | 26/11 | ATEC | 10 | 53 | 90 | 40 | 60 |
| 16 | 31 | EC/EuRSPO | 26/11 | ATBC | 10 | 53 | 92 | 80 | 54 |
| 17 | 35 | EC-7 | 10 | TL/BeesWax | 28/10 | 52 | 70 | 10 | 65 |
| 18 | 36 | EC-7 | 10 | TL/Lanolin | 28/10 | 52 | 88 | 80 | 54 |
| 19 | 37 | EC-7 | 10 | TL/Triisostearin | 28/10 | 52 | 89 | 40 | 54 |
| 20 | 38 | EC-7 | 10 | TL/Isostearin Isostearate | 28/10 | 52 | 86 | 90 | 54 |
| 21 | 39 | EC-7 | 10 | TL/Abil Wax | 28/10 | 52 | 85 | 100 | 55 |
| 22 | 41 | EC-45 | 10 | TL | 38 | 52 | 86 | 40 | 52 |
| 23 | 42 | EC-7/EC-45 | 7/3 | TL | 38 | 52 | 95 | 20 | 52 |

*samples which were tested in SEM
PMMA—poly(methyl methacrylate) co-methacrylic acid, EuRSPO—Eudragit RSPO ®, EC—ethyl cellulose.

Example 4. Preparation of Gel Formulations Comprising BPO Microcapsules

Geogard (0.7 g; a preservative combining the activity of three different preservative routes—acids, alcohols and quaternary ammonium compounds) was dissolved in water (100 g) by heating to 50-60° C. Xanthan gum (1 g) was slowly added under medium mixing until the xanthan gum gel was formed. BPO microcapsules were then added to the gel by simple mixing.

Example 5. Scanning Electron Microscopy Images of Free BPO and BPO Microcapsules 5.1 Preparation of PMMA-BPO Microcapsules:

microcapsules comprising 66% BPO and 34% PMMA (sample 2 in table 4 above) were prepared as detailed above in Examples 1 and 2. The microcapsules exhibited mean particle size of 50 μm.

5.2 Preparation of Ethyl Cellulose-BPO Microcapsules:

microcapsules comprising 66% BPO, 1% TEC and 33% Ethyl Cellulose (sample 10 in table 4 above) were prepared as detailed above in Examples 1 and 2. The microcapsules exhibited mean particle size of 50 μm.

5.3 Preparation of Trilaurin-Ethyl Cellulose-BPO Microcapsules:

microcapsules comprising 52% BPO, 18% trilaurin, 1% ATBC and 29% Ethyl Cellulose (sample 16 in table 4 above) were prepared as detailed above in Examples 1 and 2. The microcapsules exhibited mean particle size of 50 μm.

5.4 Preparation of Trilaurin-Ethyl Cellulose-BPO Microcapsules:

microcapsules comprising 55% BPO, 30% trilaurin and 15% Ethyl Cellulose (sample 21 in table 4 above) were prepared as detailed above in Examples 1 and 2. The microcapsules exhibited mean particle size of 40 μm.

5.5 Preparation of Gel Formulation Comprising BPO Microcapsules:

The xanthan gum gel was prepared as described in Example 4 above.

Figure 2A:
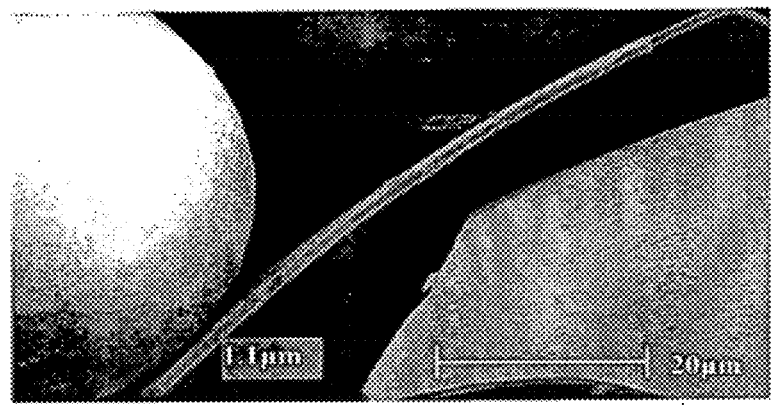
FIGS. 2A-2C show SEM images of PMMA-BPO microcapsules (sample #2) in magnifications ×4000 (2A), ×1000 (2B) and ×500 (2C). In 2A, the thickness of the shell is indicated. In 2B and 2C the diameters of exemplary microcapsules are indicated.
Figure 2B:
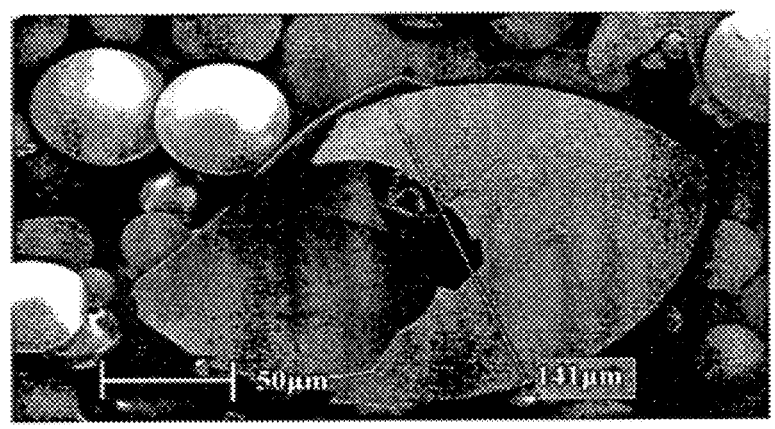
Figure 2C:
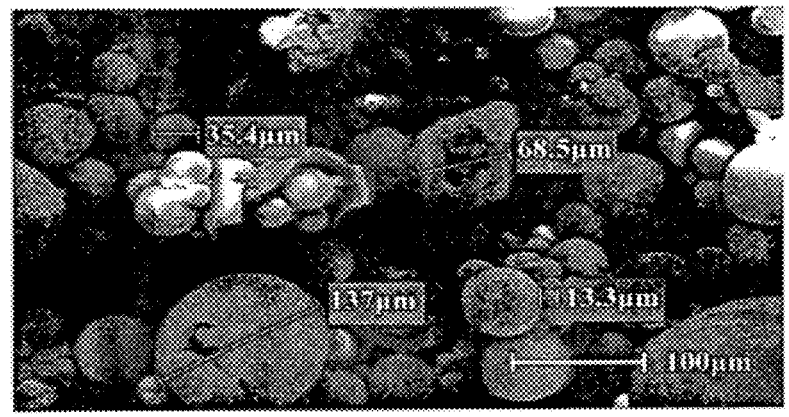
Figure 3A:
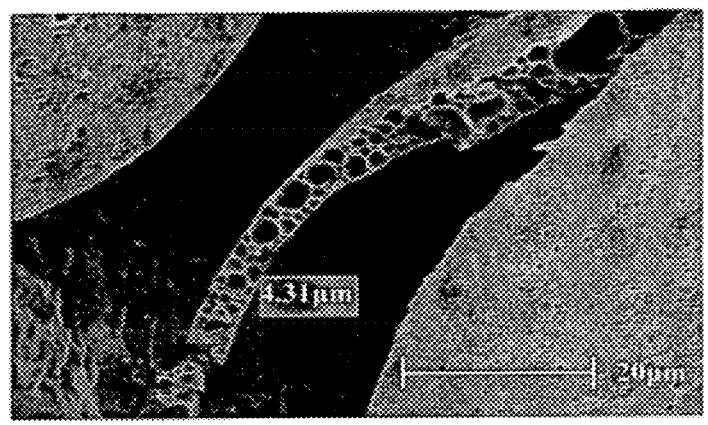
FIGS. 3A-3C show SEM images of ethyl cellulose-BPO microcapsules (sample #10) in magnifications ×4000 (3A), ×1000 (3B) and ×250 (3C). In 3A, the thickness of the shell is indicated.
Figure 3B:
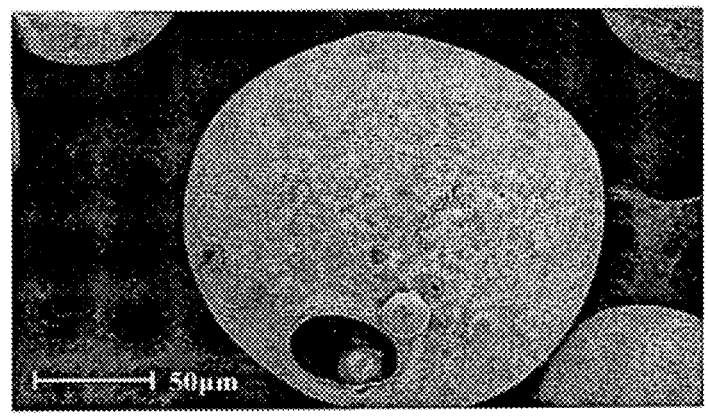
Figure 3C:
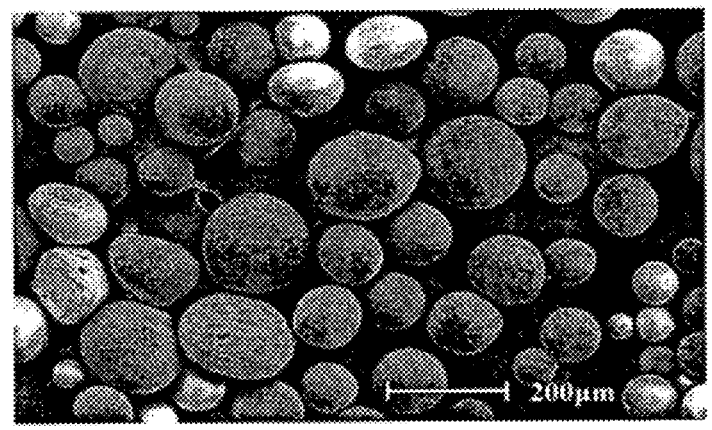
Figure 4A:
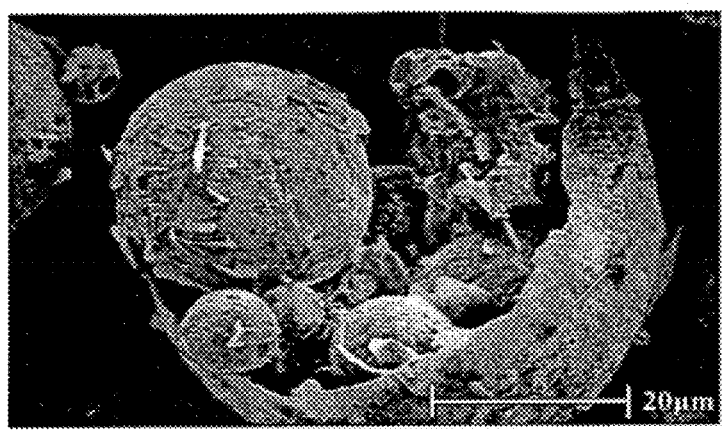
FIGS. 4A-4C show SEM images of trilaurin-ethyl cellulose-BPO microcapsules (sample #16) in magnifications ×4000 (4A), ×1000 (4B) and ×400 (4C).
Figure 4B:
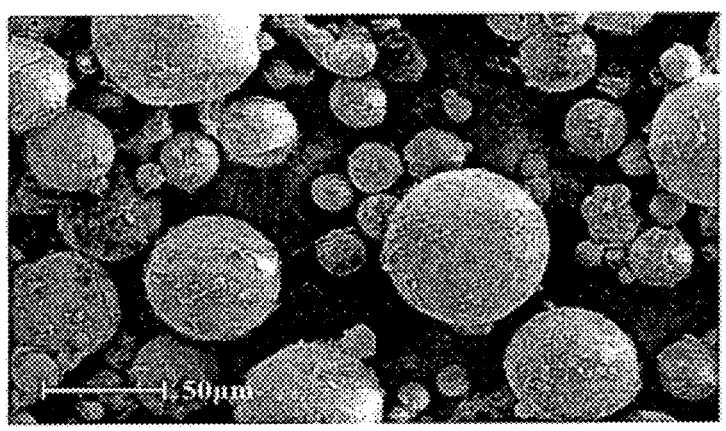
Figure 4C:
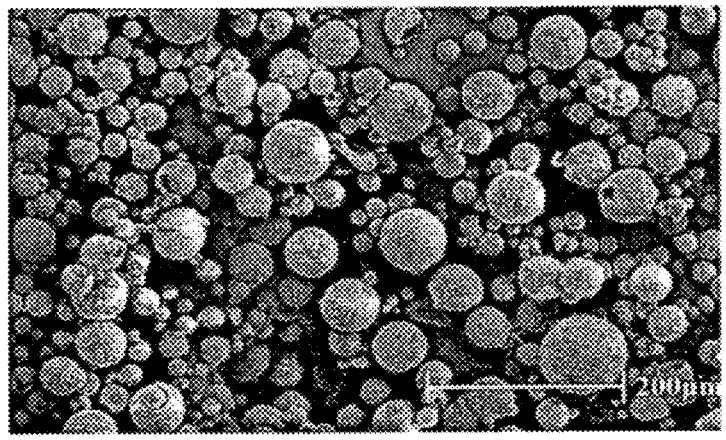
Figure 5A:
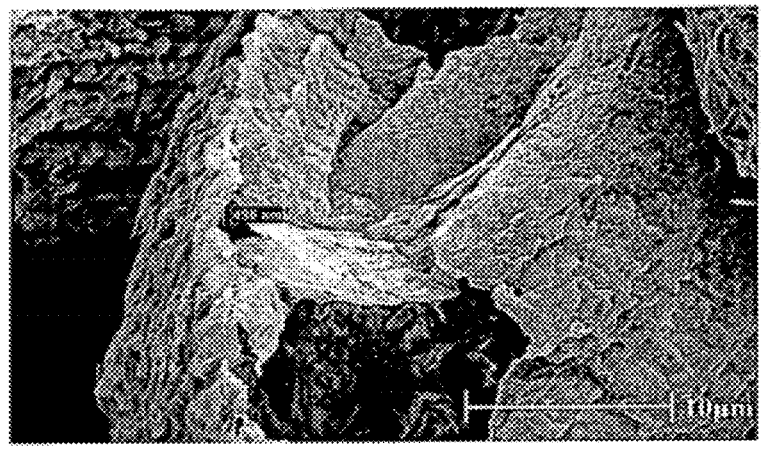
FIGS. 5A-5B show SEM images of trilaurin-ethyl cellulose-BPO (sample #21) microcapsules in magnifications ×8000 (5A) and ×400 (5B).
Figure 5B:
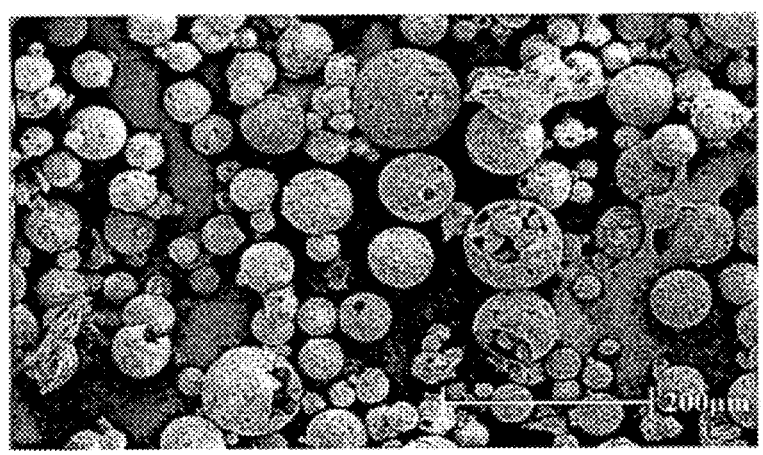

5.6 Scanning Electron Microscopy (SEM):

SEM images of free BPO indicate that the BPO particles are agglomerates (FIGS. 1A-1E). SEM images of PMMA-BPO microcapsules (prepared as detailed above in section 5.1) show that they are spherical with smooth surface (FIGS. 2A-2C). FIG. 2A shows that the microcapsules with PMMA polymeric shell have a smooth, non-porous, polymer shell with an estimated thickness of 1.1 μm. FIGS. 3A-3C, 4A-4C and 5A-5B are SEM images of the ethyl cellulose-BPO microcapsules prepared as detailed above in sections 5.2-5.4, respectively. These images show that BPO microcapsules in which the wall forming polymer is ethyl cellulose have a thicker polymeric shell (4 μm) with a rough aerated surface (non-smooth superficial surface) (FIGS. 3A-3C). In FIG. 3A it can be seen that the spherical void cavities of various diameters are smaller than the width of the shell, and thus are not conventional pores.

Example 6. BPO is Released from the Microcapsules by Rubbing Action 6.1 Preparation of PMMA-BPO Microcapsules:

microcapsules were prepared as detailed above in section 5.1 above (sample 2 in table 4 above).

6.2 Release of BPO from Microcapsules by Rubbing Action:

Light microscopic examination revealed intact particles in gel with a mean particle size of roughly 40 µm (FIG. 6A). The release of active ingredient, BPO, from capsules was accomplished via gentle pressure exerted on the top glass microscope slide with a finger. Re-examination of the slide revealed the presence of broken and distorted microcapsules (FIG. 6B). In soft BPO microcapsules, pressure results in the complete rupture of the lipid-polymer shell, releasing all entrapped oil phase contents.

Example 7. BPO Microcapsules Protect BPO from Oxidation and Prevent Release of BPO from the Microcapsules (Qualitative Evaluation)

7.1 Preparation of PMMA-BPO Microcapsules:

microcapsules were prepared as detailed above in section 5.1 above (sample 2 in table 4 above). The microcapsules exhibited mean particle size of 50 µm.

7.2 Oxidation Sensitivity Experiments:

Azo-dye congo red was used as a model for oxidation-sensitive component, the ratio BPO/congo red=30:1(w/w).

Three comparative systems were utilized:
1—BPO microcapsules (sample 2)
2—free BPO
3—without BPO (blank)

For the preparation of (1) and (2), 9 g (ml) aqueous dispersion containing 4% (w/w) BPO (free or encapsulated) were suspended with 0.1% Tween™ 20 (polysorbate 20) and 9 g liquid vehicle and stirred in a 25 ml beaker with a magnetic stirrer. Following a mixing period of 30 minutes, the temperature of the system was raised to 50-55° C. and 1 ml of a 1% aqueous solution of congo red were added. The blank system (3) was prepared by stirring 9 ml 0.1% Tween™ 20 and 9 g liquid vehicle, and adding 1 ml of a 1% aqueous solution of congo red. After stirring the suspension for 1 minute, pictures of the three systems were taken.

It can be seen in FIG. 7 that congo red solution without BPO exhibits a red color, congo red solution with the free BPO changed its color from red to yellow due to BPO oxidation and congo red with BPO microcapsules did not change its color. FIG. 7 thus demonstrates that BPO microcapsules prevent from congo red to react with BPO and therefore protect BPO from oxidation whereas free BPO does react with the congo red indicator.

These results show that BPO is not released from the microcapsules following incubation of 30 minutes into the congo red solution since no decrease in color intensity was noted. Indeed, when free BPO was dissolved in congo red solution at the same concentration as in the microcapsules, a blenching effect was discerned immediately whereas no changing red color occurs with the microcapsules which prevented in-vitro BPO release.

Example 8. BPO Microcapsules Prevent Release of BPO from the Microcapsules (Quantitative Evaluation)

8.1 Preparation of BPO Microcapsules:

microcapsules comprising 53% BPO, 10% ethyl cellulose and 37% trilaurin (sample 20 in table 4 above) were prepared as detailed above in Examples 1 and 2. The microcapsules exhibited mean particle size of 30 µm.

8.2 Chemical Stability Test:

BPO microcapsules were incorporated into gel formulation at final BPO concentration of 5% and incubated at 40° C. over 86 days. BPO concentration was determined immediately after incorporation into gel formulation and after 86 days. Total concentration of BPO was determined by mixing 1 gr of gel with dichloromethane/methanol/acetonitrile solution. BPO concentration in water phase was determined after separation of microcapsules from gel by centrifugation. The water phase was mixed with dichloromethane/methanol/acetonitrile solution in order to extract BPO and its content was determined using HPLC.

FIG. 8 shows that after 86 days of incubation at 40° C. there is a negligible decrease in the concentration of BPO in the microcapsules. These results are also reflected in table 5. No significant diffusion was observed from microcapsules to the external medium of the formulation.

TABLE 5

| Stability of BPO microcapsules | | |
|---|---|---|
| Time (Days) | 0 | 86 |
| Total | 100% | 96.6% |
| External | Not detectable | 1.2% |

Example 9. Chemical Stability of BPO Microcapsules 9.1 Preparation of Trilaurin-Ethyl Cellulose-BPO Microcapsules:

microcapsules comprising 55% BPO, 30% trilaurin and 15% Ethyl Cellulose were prepared as detailed above in section 5.4 (sample 21 in table 4 above). The microcapsules exhibited mean particle size of 40 µm.

9.2 Chemical Stability Test:

HPLC was used for BPO analysis following storage at 40° C. (encapsulated BPO vs. free BPO in a gel formulation containing 1% free retinol). HPLC analysis results show increased stability in gel with 1% free retinol. Stability stress test results (30 days storage at 40° C.) demonstrated that relative content of encapsulated BPO in a gel formulation (with final BPO concentration of 5%) decreased to 65% from the initial concentration, while naked BPO demonstrated stronger degradation to 36% (FIG. 9).

Example 10. Antimicrobial Activity of BPO Microcapsules in Gel Formulation

Antimicrobial activity was tested using microcapsules comprising 54% BPO and 10% ethyl cellulose (sample 20 in table 4 above) in gel formulation (the gel formulation was prepared as in Example 4 above). Four groups were tested as follows:
1. Naked BPO in gel
2. BPO microcapsules in gel (sample 20)
3. Broken BPO capsules in gel
4. Gel Only All experiments were performed in triplicates. The tested microorganism (*Propionibacterium acnes* 11827: ~$10^4$ cfu (colony-forming unit)/ml) was grown on tryptic soy agar slants. After incubation, the bacteria was harvested using sterile buffer phosphate pH 7.0, to obtain a microbial count of about $10^4$ cfu/ml. 0.2 ml of the above suspension was spread on tryptic soy agar plate and put aside to dry for 20 minutes at room temperature. A sterile disc of 6 mm diameter which has been soaked in 10 µl of the tested antibacterial material was put on the microbial film, the plate was incubated at 37° C. for 1-2 days. A control experiment was performed, in which no antibacterial material was put on the microbial film. Inspection of the plates after incubation revealed that antimicrobial activity of the tested material inhibits growth of the microorganism around the disc, leaving a transparent zone around it. The diameter of the inhibition zone was measured in mms. The results are presented in table 6 and in FIG. 10.

isostearyl isostearate was used as a wax in combination with trilaurin as a plasticizer. In sample 95, propylene glycol mono palmitostearate was used as a wax without any plasticizer.

Microcapsules comprising BPO, a wall forming polymer and optionally further comprising a plasticizer and a wax (as below in table 7), were prepared according to the method detailed above in Examples 1 and 2.

TABLE 7

Additional BPO microcapsules

| | Loading raw materials, % | | | Yield, % | Mean particle size, μm | BPO HPLC, % | Loading efficiency % |
|---|---|---|---|---|---|---|---|
| Sample | Polymer | Plasticizer/Wax | BPO | | | | |
| 65 | EC-7 | 2 | — | 0 | 98 | 97 | 20 | 97 | 99 |
| 67 | EC-7 | 20 | TL/isostearyl isostearate | 15/15 | 50 | 93 | 60 | 45 | 90 |
| 75 | PMMA | 50 | — | 0 | 50 | 97 | 30 | 49 | 98 |
| 77 | EC-45 | 10 | — | 0 | 90 | 97 | 30 | 88 | 97.7 |
| 81 | EC-7 | 20 | TL | 20 | 60 | 96 | 40 | 60 | 100 |
| 90 | EC-7 | 10 | TL | 10 | 80 | 96 | 33 | 78.4 | 98 |
| 91 | EC-7 | 10 | — | 0 | 90 | 97 | 30 | 87.3 | 97 |
| 92 | EC-45 | 5 | — | 0 | 95 | 94 | 35 | 88.4 | 93 |
| 93 | PMMA | 10 | TL/isostearyl isostearate | 5/5 | 80 | 97 | 35 | 78.4 | 98 |
| 95 | EC-7 | 10 | PGMP | 10 | 80 | 95 | 30 | 77.6 | 97 |

PMMA—poly(methyl methacrylate) co-methacrylic acid, EC—ethyl cellulose.

TABLE 6

Propionibacterium acnes 11827 growth inhibition

| Samples | Inhibition diameter (mm) |
|---|---|
| Control | 0, 0, 0 |
| Naked BPO in gel | 8, 8, 6 |
| BPO capsules in gel | 6, 6, 10 |
| Broken BPO capsules in gel | 12, 15, 17 |
| Gel Only | 0, 6, 0 |

Figure 10:
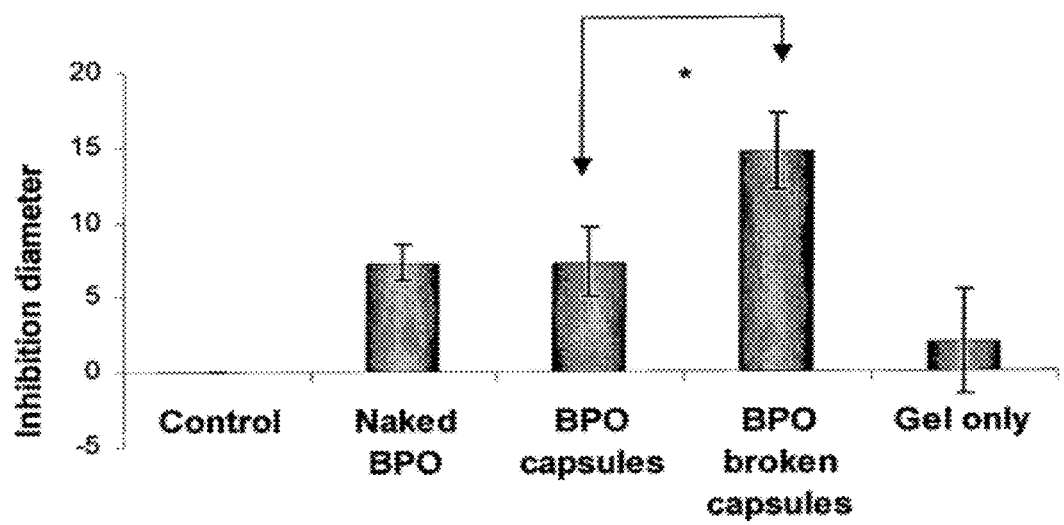
FIG. 10 shows BPO antimicrobial activity following incubation over a period of 1-2 days at 37° C. Values are average ±SD. N=3. * indicates that the P value of Tukey-Kramer Multiple Comparisons was at least 0.05.
Figure 11A:
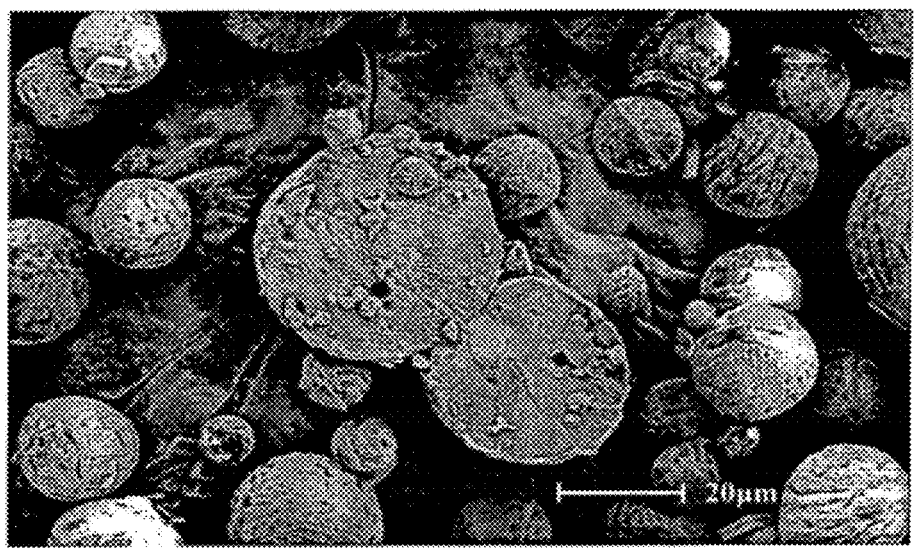
FIGS. 11A-11B show SEM images of ethyl cellulose-BPO microcapsules (sample #65) in magnifications ×2000 (11A) and ×1000 (11B). In 11B the diameters of exemplary microcapsules are indicated.
Figure 11B:
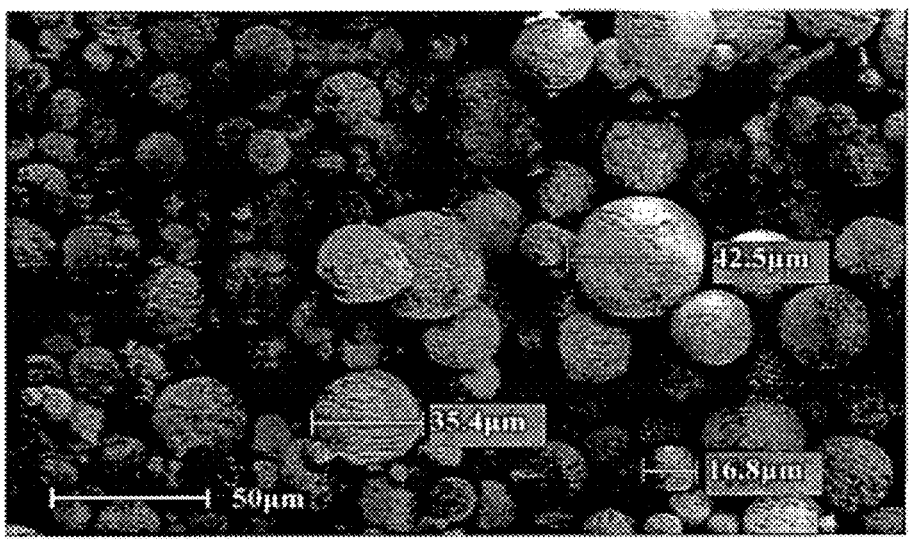
Figure 12A:
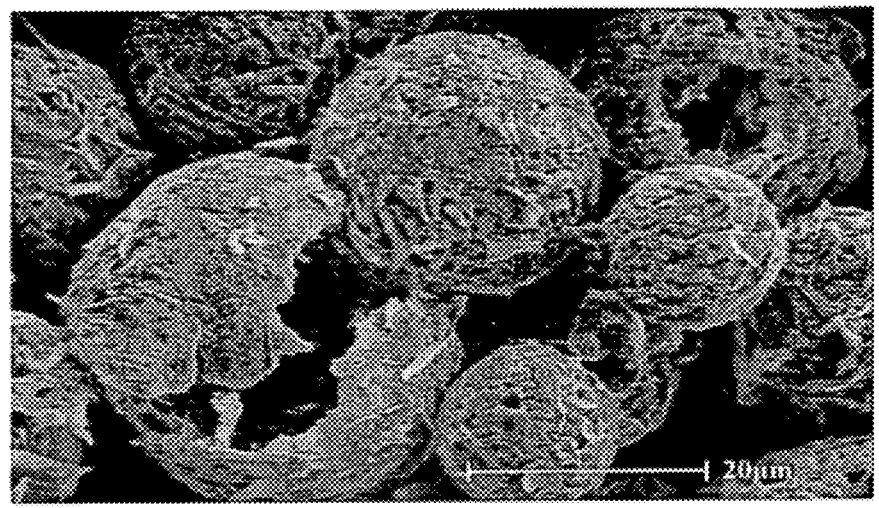
FIGS. 12A-12B show SEM images of ethyl cellulose-BPO microcapsules (sample #67) in magnifications ×4000 (12A) and ×500 (12B). In 12B the diameters of exemplary microcapsules are indicated.
Figure 12B:
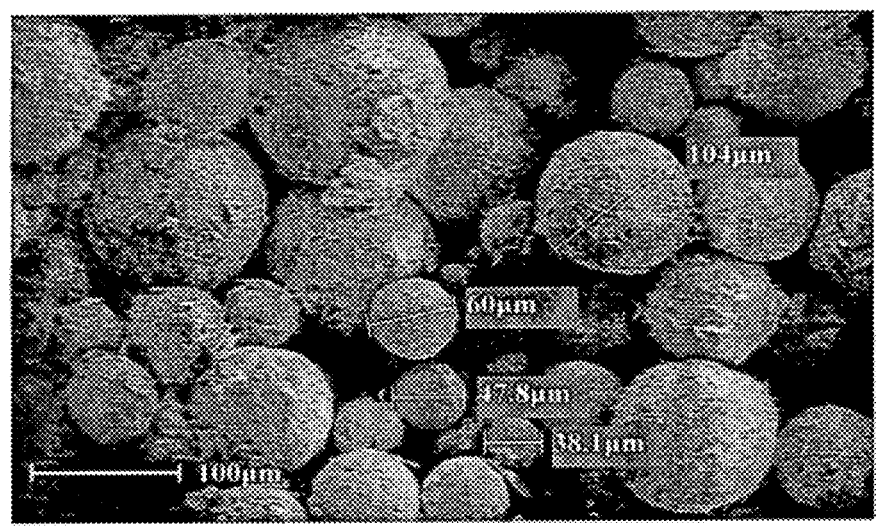
Figure 13A:
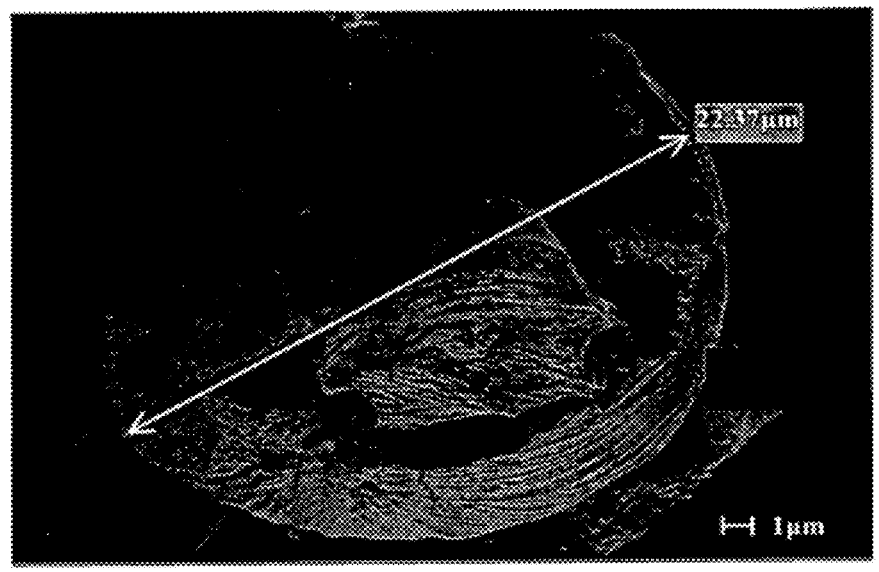
FIGS. 13A-13B show SEM images of PMMA-BPO microcapsules (sample #75) in magnifications ×10000 (13A) and ×1000 (13B). In 13B the diameter of an exemplary microcapsule is indicated.
Figure 13B:
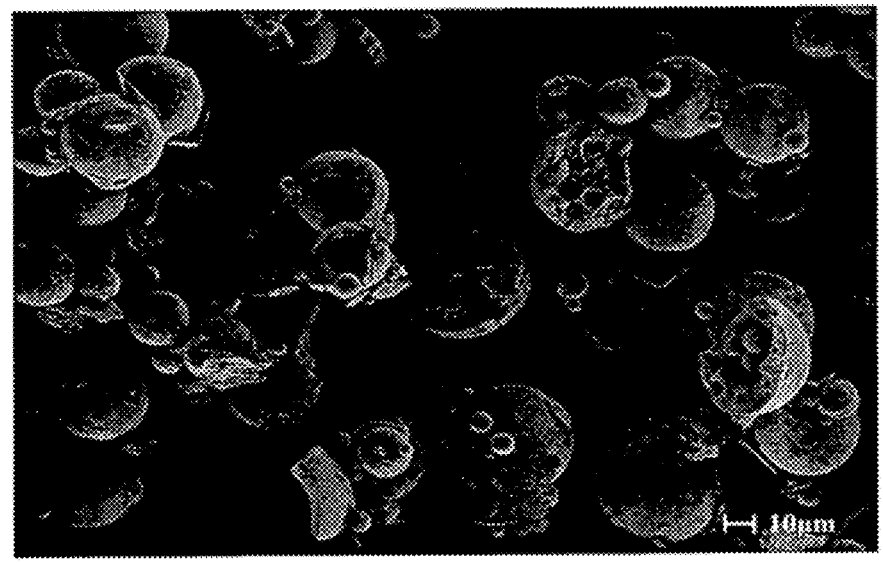
Figure 14A:
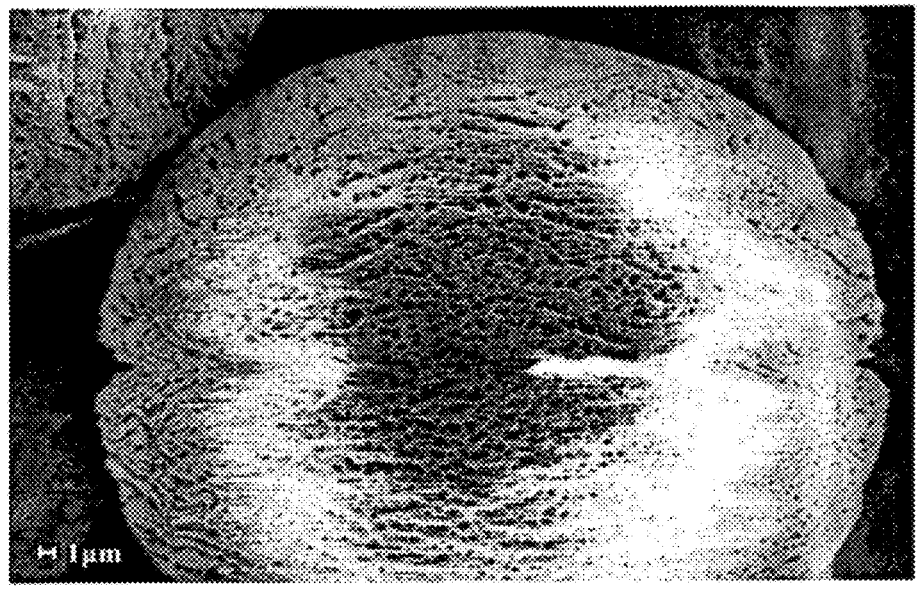
FIGS. 14A-14B show SEM images of ethyl cellulose-BPO microcapsules (sample #77) in magnifications ×5000 (14A) and ×500 (14B).
Figure 14B:
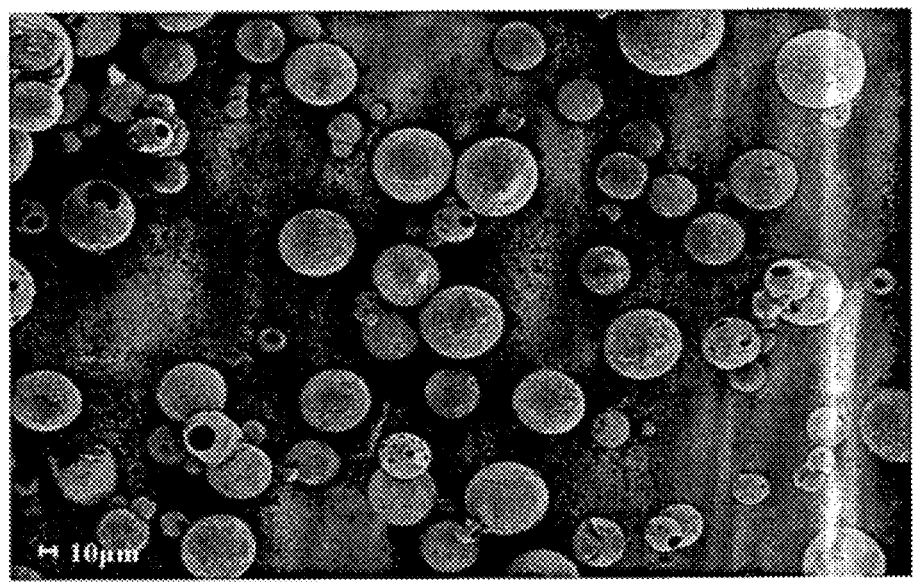
Figure 15A:
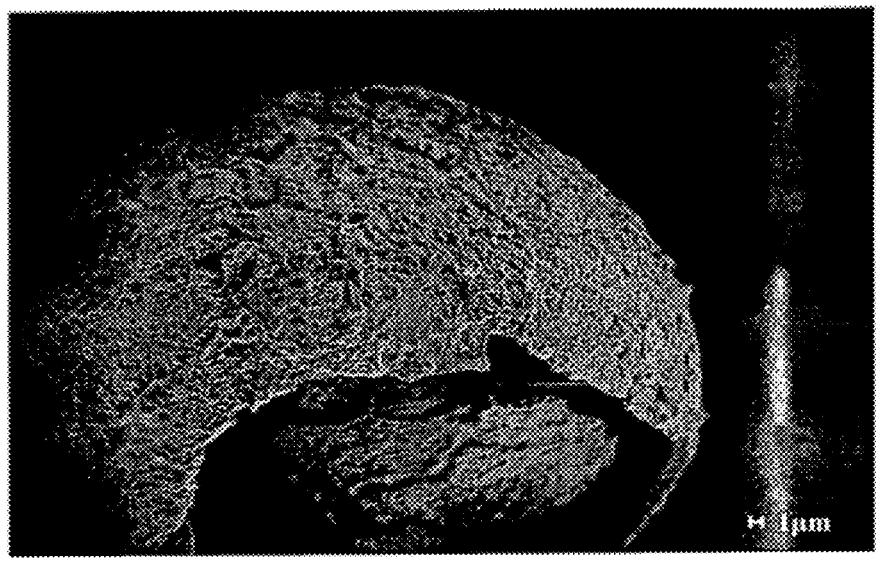
FIGS. 15A-15B show SEM images of ethyl cellulose-BPO microcapsules (sample #81) in magnifications ×5000 (15A) and ×1000 (15B).
Figure 15B:
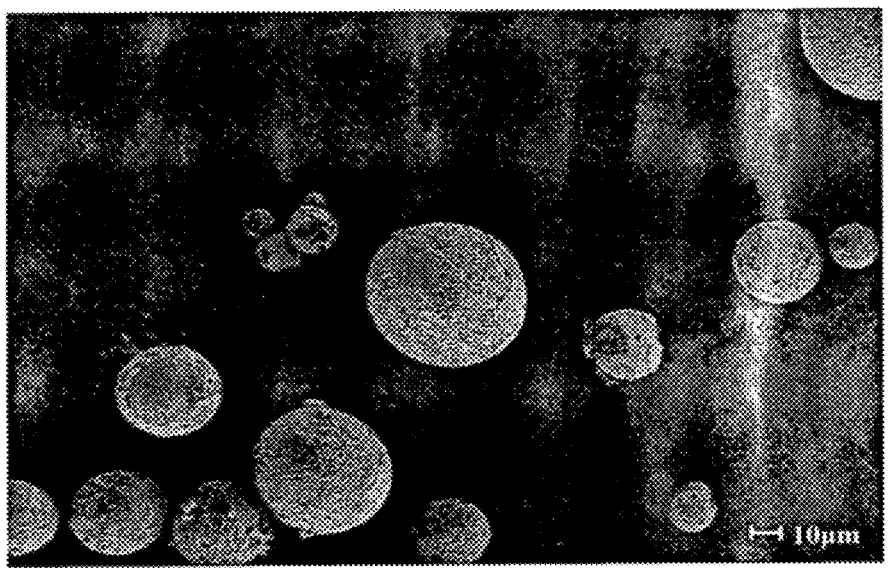
Figure 16A:
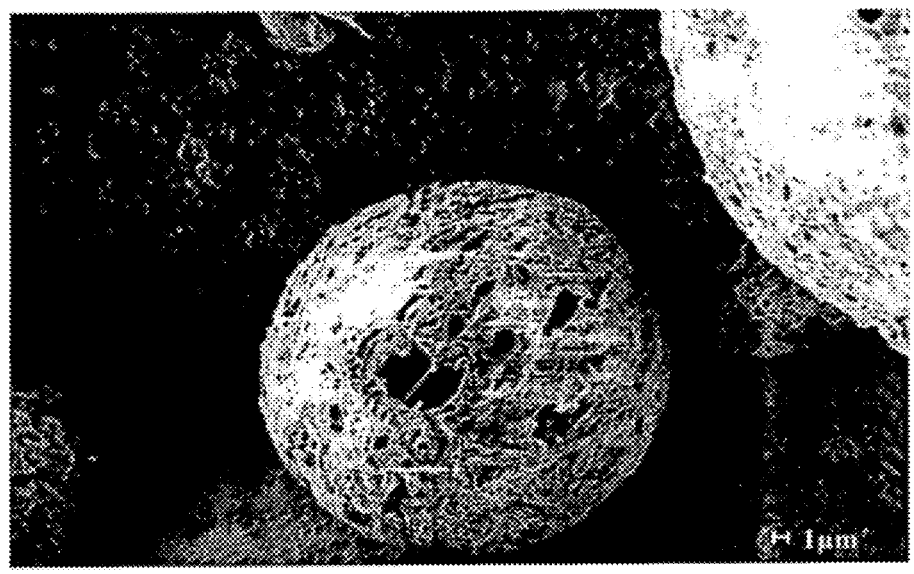
FIGS. 16A-16B show SEM images of ethyl cellulose-BPO microcapsules (sample #90) in magnifications ×5000 (16A) and ×1000 (16B). In 16B the diameters of exemplary microcapsules are indicated.
Figure 16B:
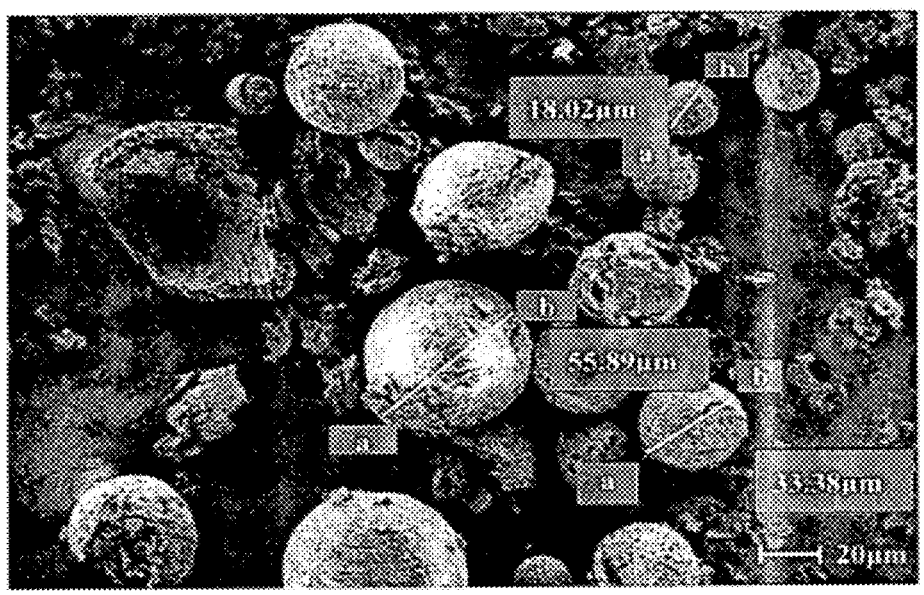
Figure 17A:
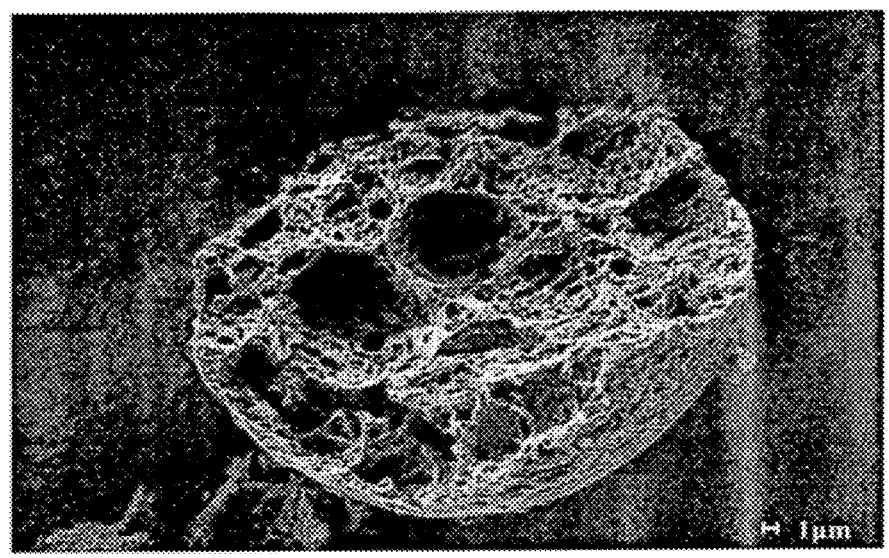
FIGS. 17A-17B show SEM images of ethyl cellulose-BPO microcapsules (sample #91) in magnifications ×5000 (17A) and ×1000 (17B). In 17B the diameters of exemplary microcapsules (distance from a to b) are indicated.
Figure 17B:
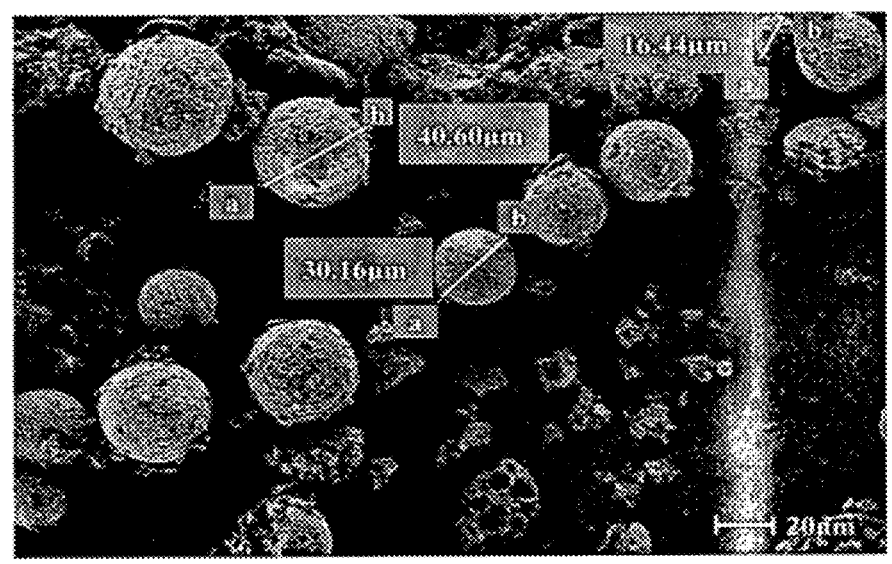
Figure 18A:
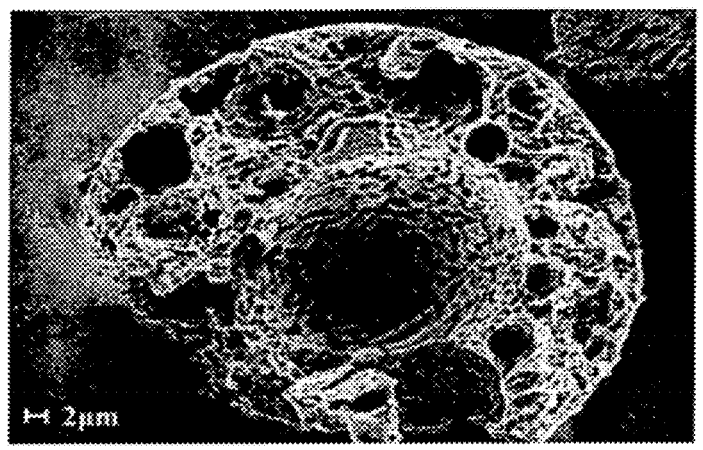
FIGS. 18A-18C show SEM images of ethyl cellulose-BPO microcapsules (sample #92) in magnifications ×5000 (18A), ×5000 (18B) and ×1000 (18C). In 18C the diameters of exemplary microcapsules (distance from a to b) are indicated.
Figure 18B:
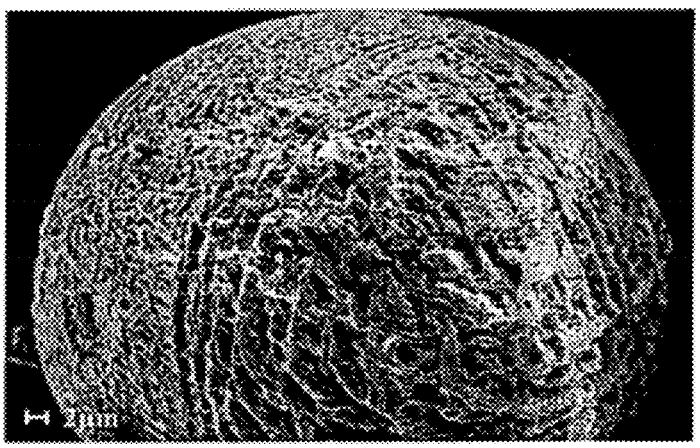
Figure 18C:
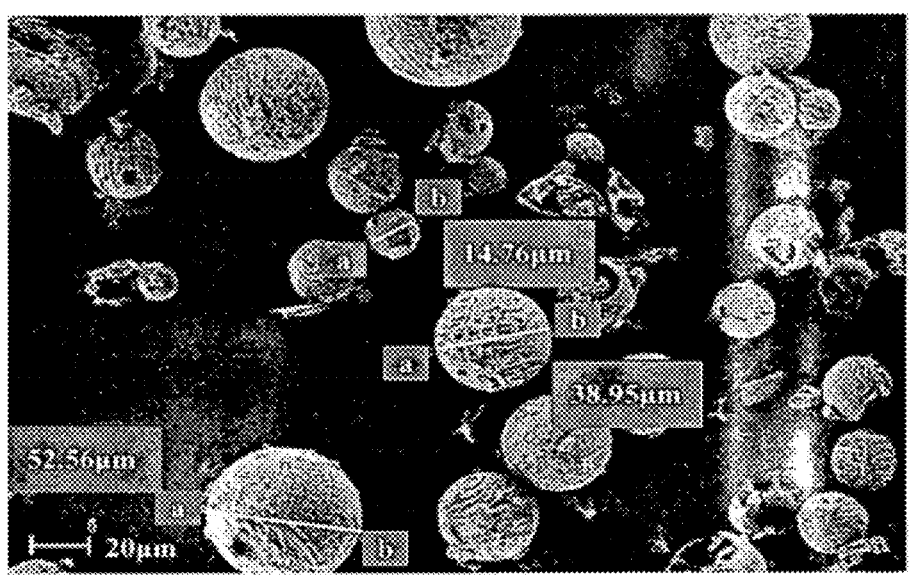
Figure 19A:
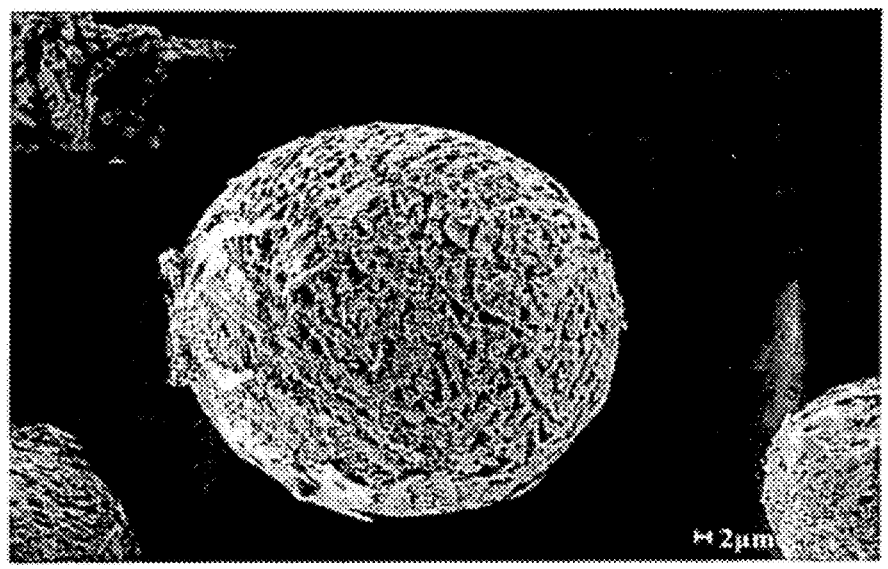
FIGS. 19A-19B show SEM images of PMMA-BPO microcapsules (sample #93) in magnifications ×5000 (19A) and ×1000 (19B). In 19B the diameters of exemplary microcapsules (distance from a to b) are indicated.
Figure 19B:
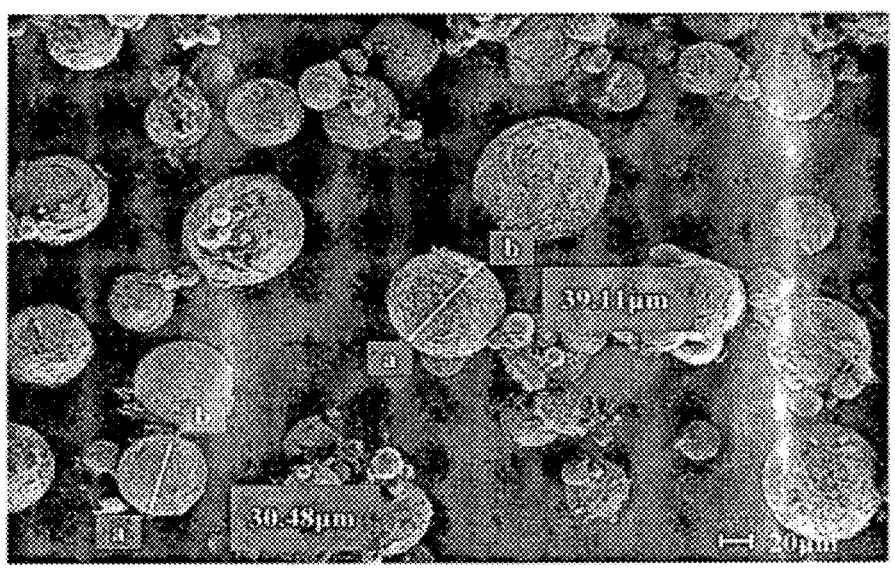
Figure 20A:
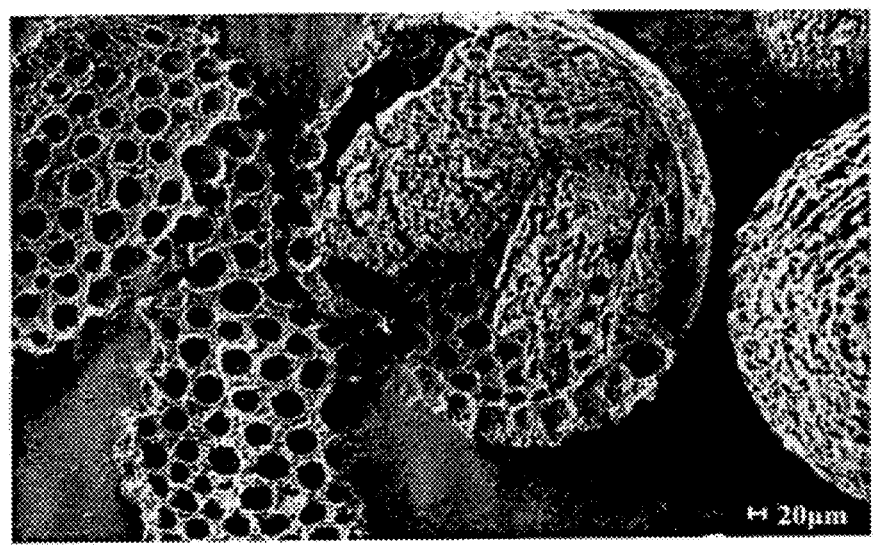
FIGS. 20A-20B show SEM images of ethyl cellulose-BPO microcapsules (sample #95) in magnifications ×5000 (20A) and ×1000 (20B). In 20B the diameters of exemplary microcapsules (distance from a to b) are indicated.
Figure 20B:
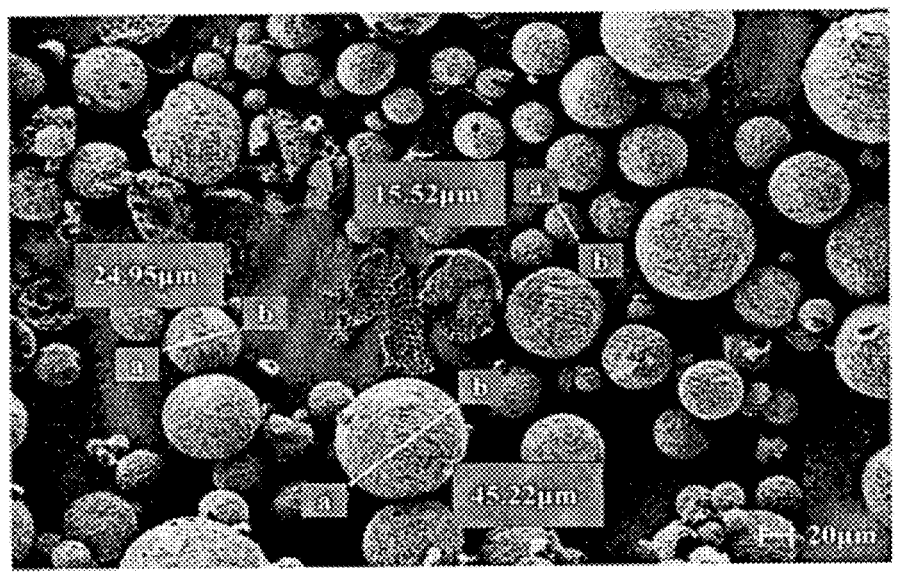

The results presented in table 6 and in FIG. 10, clearly show that broken BPO microcapsules in gel are most effective in inhibiting bacteria growth, even more effective than naked BPO in gel formulation. These results indicate that gel formulations comprising BPO microcapsules would be effective in treating acne when rubbed on the skin. The P value of Tukey-Kramer Multiple Comparisons between the groups of BPO capsules and broken BPO capsules was at least 0.05, which indicates a statistically significant difference between the two groups.

Example 11. Preparation of Additional BPO Microcapsules

Additional types of microcapsules comprising higher loads of BPO were prepared using the procedure detailed above in Examples 1 and 2. The composition, mean particle size and BPO content of the different microcapsules are detailed in Table 7 below.

The wall-forming polymer used was ethyl cellulose (EC-7 or EC-45) in samples 65, 67, 77, 81, 90, 91, 92 and 95, or poly(methyl methacrylate) co-methacrylic acid (PMMA) in samples 75 and 93. In samples 65, 75, 77, 91, 92 and 95 no plasticizer was used. In samples 67, 81, 90 and 93 trilaurin (TL) was used as a plasticizer. In samples 67 and 93

Example 12. Scanning Electron Microscopy Images of the BPO Microcapsules

Scanning electron microscopy (SEM) images of the BPO microcapsules (prepared as detailed above in Example 11) were taken using Zeiss Ultra Gemini® (Zeiss, Germany). SEM images show that all microcapsules have a spherical shape and a rough aerated surface (non-smooth superficial surface, FIGS. 11A-11B, 12A-12B, 13A-13B, 14A-14B, 15A-15B, 16A-16B, 17A-17B, 18A-18C, 19A-19B and 20a-20B). In FIGS. 3A, 13A, 17A, 18A and 20A, it can be seen that the spherical void cavities in the shell do not span the whole width of the shell, and thus are not conventional pores.

Example 13. Stability Tests of the BPO Microcapsules 13.1 Preparation of Aqueous Gel Formulations Comprising BPO Microcapsules:

Geogard (0.7 g, Lonza) was dissolved in water by heating to 40-50° C. and the solution was allowed to cool to room temperature. Clindamycin phosphate was optionally dissolved in the solution (in formulations comprising antibiotics). Xanthan gum (1 g, Interaxion) was slowly added under medium mixing until the xanthan gum gel was formed. BPO microcapsules were then added to the gel by simple mixing. The composition of the gel formulation is detailed in Table 8 below.

TABLE 8 composition of xanthan gum gel:

| # | Ingredient | Gel Base (%) | Gel Base + Antibiotic (%) |
|---|---|---|---|
| 1 | Geogard Ultra—Preservative | 0.7 | 0.7 |
| 2 | Xanthan Gum | 1 | 1 |
| 3 | Water | 98.3 | 97.3 |
| 4 | Clindamycin phosphate | — | 0.75-1 |

13.2 Chemical Stability of BPO in Aqueous Gel Formulation:

BPO microcapsules were incorporated into the gel formulation (gel base comprising no clindamycin) at final BPO concentration of 5% and incubated at 40° C. over 90 days. Stability studies were performed for compositions comprising only encapsulated BPO or encapsulated BPO in combination with 0.75-1% of Clindamycin Phosphate. BPO concentration was determined immediately after incorporation into gel formulation and after 30, 60 and 90 days. Total concentration of BPO was determined by mixing 1 gr of the gel formulation with dichloromethane/methanol/acetonitrile solution. BPO concentration in water phase was determined after separation of microcapsules from gel by centrifugation. The water phase was mixed with dichloromethane/methanol/acetonitrile solution in order to extract BPO and its content was determined using HPLC.

FIG. 21 shows that after 90 days of incubation at 40° C. there is a negligible decrease in the concentration of BPO in gel formulations comprising BPO microcapsules and also in formulations comprising non-encapsulated BPO.

13.3 Chemical Stability of Clindamycin Phosphate in Aqueous Gel Formulations Comprising BPO Microcapsules:

BPO microcapsules (prepared as detailed above in Example 11) were incorporated into the gel formulation (comprising 0.75-1% clindamycin phosphate) at final BPO concentration of 5% and incubated at 40° C. over 90 days. Total clindamycin phosphate concentration was determined immediately after incorporation into gel formulation and after 30, 60 and 90 days, using HPLC. In addition, clindamycin phosphate concentration was measured in a similar manner in two commercial products comprising both BPO and 1% clindamycin (trade product 1 and trade product 2) which were also incubated at 40° C. over 90 days.

Figure 22A:
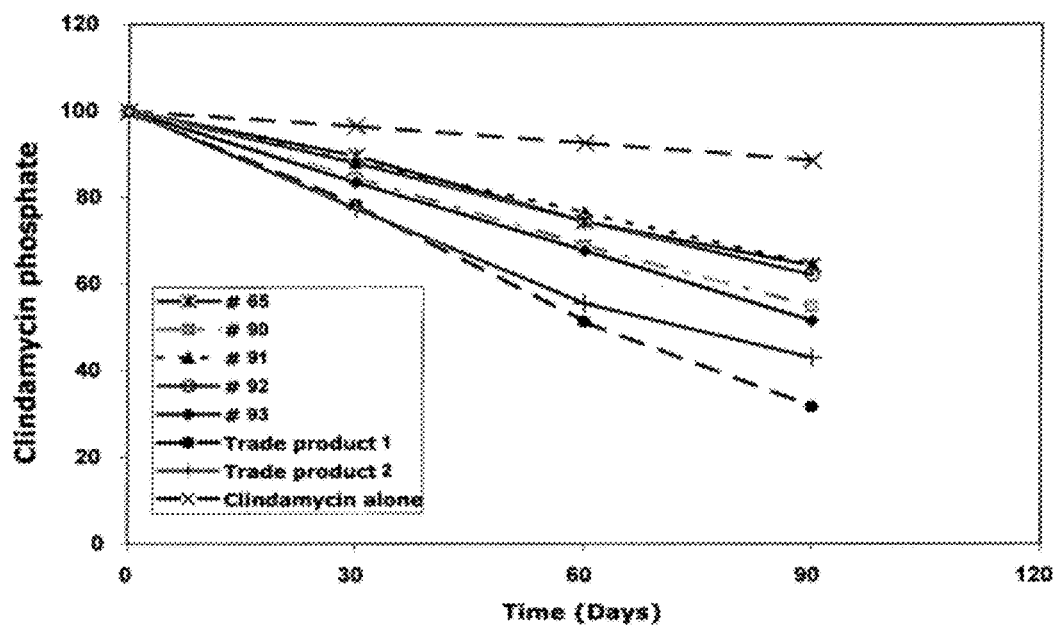
FIGS. 22A-22B show the stability of clindamycin phosphate in aqueous gel formulations comprising BPO microcapsules (samples #65, #90, #91, #92 and #93) as compared to that in trade products and to clindamycin phosphate alone. (22A) In the aqueous gel formulations comprising BPO microcapsules the clindamycin phosphate was 50-100% more sable than in commercial trade products 1 and 2. (22A) Increasing the loading of BPO in microcapsules results in increased stability of clindamycin phosphate after 30 days incubation at 40° C.
Figure 22B:
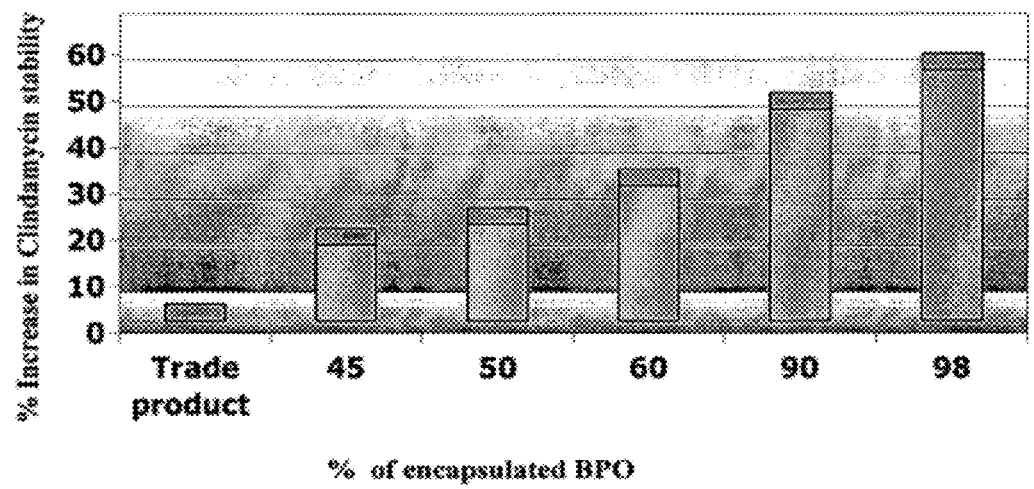

FIG. 22A shows that the concentration of clindamycin phosphate is 50-100% more stable in aqueous gel formulations comprising BPO microcapsules as compared to trade products 1 and 2. FIG. 22B shows that the higher the loading of BPO in the microcapsules the higher the stability of clindamycin phosphate in the composition, after 30 days incubation at 40° C.

Example 14. Dermatology Irritation Tests

BPO microcapsules (samples #65, #90, #91, #92 and #93, prepared as detailed above in Example 11) were incorporated into the gel formulation (prepared as in Example 13.1 above) at final BPO concentration of 5% (w:w). 0.07-0.1 ml or gr. of the tested composition was applied in a patch test (Finn Chamber/Hill Top Chamber/Leukotest or any other similar chamber).

The tests were conducted on 50 volunteers with normal, non-diseased skin, on the intrascapular region of the back, or the dorsal surface of the upper arm. Patches were secured in place with surgical tape without wrapping the trunk or arm. In the single patch test design, after 48 hours of a single exposure, test patches were removed and the test area was marked for evaluation. Evaluation of the response was performed 1 hr, 24 hrs, and 48 hrs after patch removal.

Reactions were graded as follows: 0—negative, normal skin; +—questionable erythema not covering entire area; 1—definite erythema; 2—erythema and induration; 3—vesiculation; 4—bullous reaction. The test was acceptable only when there were no reactions (0 on the scale).

Our results show that in all tested samples, no reaction (irritation) was observed in any of the volunteers. Exemplary results for samples #65 and #90 are shown in Tables 9 and 10, respectively.

TABLE 9

Dermatology test results for sample #65

| No. | Subject | Sex | Age | 1 hr after removal | 24 hrs after removal | 48 hrs after removal |
|---|---|---|---|---|---|---|
| 1 | B. Y | F | 49 | 0 | 0 | 0 |
| 2 | H. M | M | 59 | 0 | 0 | 0 |
| 3 | G. A | F | 53 | 0 | 0 | 0 |
| 4 | G. G | M | 32 | 0 | 0 | 0 |
| 5 | G. M | M | 35 | 0 | 0 | 0 |
| 6 | G. D | F | 19 | 0 | 0 | 0 |
| 7 | H. A | F | 55 | 0 | 0 | 0 |
| 8 | C. R | F | 38 | 0 | 0 | 0 |
| 9 | C. G | M | 38 | 0 | 0 | 0 |
| 10 | H. E | F | 58 | 0 | 0 | 0 |
| 11 | S. R | F | 49 | 0 | 0 | 0 |
| 12 | C. M | M | 57 | 0 | 0 | 0 |
| 13 | S. S | F | 60 | 0 | 0 | 0 |
| 14 | P. S | F | 60 | 0 | 0 | 0 |
| 15 | P. S | M | 62 | 0 | 0 | 0 |
| 16 | P. V | F | 53 | 0 | 0 | 0 |
| 17 | O. S | F | 30 | ± | 0 | 0 |
| 18 | O. L | F | 32 | 0 | 0 | 0 |
| 19 | E. H | F | 34 | 0 | 0 | 0 |
| 20 | S. G | F | 31 | 0 | 0 | 0 |
| 21 | R. A | M | 33 | 0 | 0 | 0 |
| 22 | Y. H | M | 35 | 0 | 0 | 0 |
| 23 | Y. L | F | 54 | 0 | 0 | 0 |
| 24 | S. G | F | 45 | 0 | 0 | 0 |
| 25 | I. G | M | 50 | 0 | 0 | 0 |
| 26 | G. C | F | 32 | 0 | 0 | 0 |
| 27 | B. B | F | 38 | 0 | 0 | 0 |
| 28 | G. G | M | 26 | 0 | 0 | 0 |
| 29 | P. Z | F | 50 | 0 | 0 | 0 |
| 30 | P. N | M | 52 | ± | 0 | 0 |
| 31 | P. B | F | 19 | 0 | 0 | 0 |
| 32 | P. M | F | 23 | 0 | 0 | 0 |
| 33 | S. O | M | 45 | 0 | 0 | 0 |
| 34 | A. M | F | 45 | 0 | 0 | 0 |
| 35 | R. A | F | 45 | 0 | 0 | 0 |
| 36 | R. T | F | 19 | 0 | 0 | 0 |
| 37 | M. O | F | 50 | 0 | 0 | 0 |
| 38 | B. S | F | 50 | 0 | 0 | 0 |
| 39 | A. H | F | 40 | 0 | 0 | 0 |
| 40 | G. A | F | 49 | 0 | 0 | 0 |
| 41 | S. S | F | 19 | 0 | 0 | 0 |
| 42 | S. T. | M | 28 | 0 | 0 | 0 |
| 43 | S. I. | M | 26 | 0 | 0 | 0 |
| 44 | T. S | F | 22 | 0 | 0 | 0 |
| 45 | S. R | M | 58 | 0 | 0 | 0 |
| 46 | S. M | F | 27 | 0 | 0 | 0 |
| 47 | M. N | F | 42 | 0 | 0 | 0 |
| 48 | T. T | F | 40 | 0 | 0 | 0 |
| 49 | L. M | F | 29 | 0 | 0 | 0 |
| 50 | R. V | F | 43 | 0 | 0 | 0 |

TABLE 10

Dermatology test results for sample #90

| No. | Subject | Sex | Age | 1 hr after removal | 24 hrs after removal | 48 hrs after removal |
|---|---|---|---|---|---|---|
| 1 | B. Y | F | 49 | 0 | 0 | 0 |
| 2 | H. M | M | 59 | 0 | 0 | 0 |
| 3 | G. A | F | 53 | 0 | 0 | 0 |
| 4 | G. G | M | 32 | 0 | 0 | 0 |
| 5 | G. M | M | 35 | 0 | 0 | 0 |
| 6 | G. D | F | 19 | 0 | 0 | 0 |
| 7 | H. A | F | 55 | 0 | 0 | 0 |
| 8 | C. R | F | 38 | 0 | 0 | 0 |
| 9 | C. G | M | 38 | 0 | 0 | 0 |
| 10 | H. E | F | 58 | 0 | 0 | 0 |
| 11 | S. R | F | 49 | 0 | 0 | 0 |
| 12 | C. M | M | 57 | 0 | 0 | 0 |
| 13 | S. S | F | 60 | 0 | 0 | 0 |
| 14 | P. S | F | 60 | 0 | 0 | 0 |
| 15 | P. S | M | 62 | 0 | 0 | 0 |
| 16 | P. V | F | 53 | 0 | 0 | 0 |
| 17 | O. S | F | 30 | 0 | 0 | 0 |
| 18 | O. L | F | 32 | 0 | 0 | 0 |
| 19 | E. H | F | 34 | 0 | 0 | 0 |
| 20 | S. G | F | 31 | 0 | 0 | 0 |
| 21 | R. A | M | 33 | 0 | 0 | 0 |
| 22 | Y. H | M | 35 | 0 | 0 | 0 |
| 23 | Y. L | F | 54 | 0 | 0 | 0 |
| 24 | S. G | F | 45 | 0 | 0 | 0 |
| 25 | I. G | M | 50 | 0 | 0 | 0 |
| 26 | G. C | F | 32 | 0 | 0 | 0 |
| 27 | B. B | F | 38 | 0 | 0 | 0 |
| 28 | G. G | M | 26 | 0 | 0 | 0 |
| 29 | P. Z | F | 50 | 0 | 0 | 0 |
| 30 | P. N | M | 52 | 0 | 0 | 0 |
| 31 | P. B | F | 19 | 0 | 0 | 0 |
| 32 | P. M | F | 23 | 0 | 0 | 0 |
| 33 | S. O | M | 45 | 0 | 0 | 0 |
| 34 | A. M | F | 45 | 0 | 0 | 0 |
| 35 | R. A | F | 45 | 0 | 0 | 0 |
| 36 | R. T | F | 19 | 0 | 0 | 0 |
| 37 | M. O | F | 50 | 0 | 0 | 0 |
| 38 | B. S | F | 50 | 0 | 0 | 0 |
| 39 | A. H | F | 40 | 0 | 0 | 0 |
| 40 | G. A | F | 49 | 0 | 0 | 0 |
| 41 | S. S | F | 19 | 0 | 0 | 0 |
| 42 | S. T | M | 28 | 0 | 0 | 0 |
| 43 | S. I | M | 26 | 0 | 0 | 0 |
| 44 | T. S | F | 22 | 0 | 0 | 0 |
| 45 | S. R | M | 58 | 0 | 0 | 0 |
| 46 | S. M | F | 27 | 0 | 0 | 0 |
| 47 | M. N | F | 42 | 0 | 0 | 0 |
| 48 | T. T | F | 40 | 0 | 0 | 0 |
| 49 | L. M | F | 29 | 0 | 0 | 0 |
| 50 | R. V | F | 43 | 0 | 0 | 0 |

Example 15. Draize Repeated Insult Patch Test (RIM) Tests

Sensitizing properties of the wall forming polymers and the additives were determined by Draize repeated insult patch test in human volunteers. Empty microcapsules (corresponding to samples #90 and #93) were prepared as detailed above in Example 11 with no BPO, and incorporated into gel formulations (prepared as in Example 13.1 above). 0.07-0.1 ml or gr. of the tested composition was applied in a patch test (Finn Chamber/Hill Top Chamber/Leukotest or any other similar chamber).

The tests were conducted on 50 volunteers with normal, non-diseased skin, on the intrascapular region of the back, or the dorsal surface of the upper arm. Patches were secured in place with surgical tape without wrapping the trunk or arm.

In the induction phase, the patch was applied to its designated contact site and remained in place for 24 hours. At the end of this period the patch was removed and the site was examined for any dermal response. The volunteers then rested for 24 hours, after which the skin site was examined again. A patch was then applied to the same site as previously used. The second application was identical to the first and remained in place for 24 hours. This procedure was repeated until a series of nine applications was completed. The same site was used throughout the study. The site of application was then evaluated for any dermal response prior to the next (tenth) application.

In the challenge phase, following a rest period of 2 weeks (after the 9th application) a challenge application was applied in the same manner and to the same site as described above. The challenge application was removed after 24 hours and the site was examined and graded for signs of irritation or sensitization. A follow-up examination was conducted at 48 hours after the challenge application (24 hours after patch removal), as well as at 48 hours after patch removal.

The results depicted below in Tables 11 and 12 show that both microcapsule prototypes did not induce in the 10th application (challenge phase) a contact dermal irritation and/or sensitization in human subjects.

TABLE 11

RIPT test results for empty microcapsules corresponding to sample #90.

| No. | Subject | Sex | Age | 20 min after removal of $10^{th}$ application | 24 hrs after removal of $10^{th}$ application | 48 hrs after removal of $10^{th}$ application |
|---|---|---|---|---|---|---|
| 1 | B. Y | F | 49 | 0 | 0 | 0 |
| 2 | H. M | M | 59 | 0 | 0 | 0 |
| 3 | G. A | F | 53 | 0 | 0 | 0 |
| 4 | G. G | M | 32 | 0 | 0 | 0 |
| 5 | G. M | M | 35 | 0 | 0 | 0 |
| 6 | G. D | F | 19 | 0 | 0 | 0 |
| 7 | H. A | F | 55 | 0 | 0 | 0 |
| 8 | C. R | F | 38 | 0 | 0 | 0 |
| 9 | C. G | M | 38 | 0 | 0 | 0 |
| 10 | H. E | F | 58 | 0 | 0 | 0 |
| 11 | C. M | M | 57 | 0 | 0 | 0 |
| 12 | S. S | F | 60 | 0 | 0 | 0 |
| 13 | P. S | F | 60 | 0 | 0 | 0 |
| 14 | P. S | M | 62 | 0 | 0 | 0 |
| 15 | P. V | F | 53 | 0 | 0 | 0 |
| 16 | O. S | F | 30 | 0 | 0 | 0 |
| 17 | O. L | F | 32 | 0 | 0 | 0 |
| 18 | E. H | F | 34 | 0 | 0 | 0 |
| 19 | S. G | F | 31 | 0 | 0 | 0 |
| 20 | R. A | M | 33 | 0 | 0 | 0 |
| 21 | Y. H | M | 35 | 0 | 0 | 0 |
| 22 | Y. L | F | 54 | 0 | 0 | 0 |
| 23 | S. G | F | 45 | 0 | 0 | 0 |
| 24 | I. G | M | 50 | 0 | 0 | 0 |
| 25 | G. C | F | 32 | 0 | 0 | 0 |
| 26 | B. B | F | 38 | 0 | 0 | 0 |
| 27 | G. G | M | 26 | 0 | 0 | 0 |
| 28 | A. U | M | 35 | 0 | 0 | 0 |
| 29 | M. H | F | 37 | 0 | 0 | 0 |
| 30 | P. Z | F | 50 | 0 | 0 | 0 |
| 31 | P. N | M | 52 | 0 | 0 | 0 |
| 32 | S. O | M | 45 | 0 | 0 | 0 |
| 33 | A. M | F | 45 | 0 | 0 | 0 |
| 34 | R. A | F | 45 | 0 | 0 | 0 |
| 35 | R. T | F | 19 | 0 | 0 | 0 |
| 36 | M. O | F | 50 | 0 | 0 | 0 |
| 37 | B. S | F | 50 | 0 | 0 | 0 |
| 38 | A. H | F | 40 | 0 | 0 | 0 |
| 39 | G. A | F | 49 | 0 | 0 | 0 |
| 40 | S. S | F | 19 | 0 | 0 | 0 |
| 41 | S. T | M | 28 | 0 | 0 | 0 |
| 42 | S. I | M | 26 | 0 | 0 | 0 |
| 43 | T. S | F | 22 | 0 | 0 | 0 |
| 44 | S. R | M | 58 | 0 | 0 | 0 |

TABLE 11-continued

RIPT test results for empty microcapsules corresponding to sample #90.

| No. | Subject | Sex | Age | 20 min after removal of 10$^{th}$ application | 24 hrs after removal of 10$^{th}$ application | 48 hrs after removal of 10$^{th}$ application |
|---|---|---|---|---|---|---|
| 45 | S. M | F | 27 | 0 | 0 | 0 |
| 46 | M. N | F | 42 | 0 | 0 | 0 |
| 47 | T. T | F | 40 | 0 | 0 | 0 |
| 48 | L. M | F | 29 | 0 | 0 | 0 |
| 49 | R. V | F | 43 | 0 | 0 | 0 |
| 50 | E. D | F | 33 | 0 | 0 | 0 |

TABLE 12

RIPT test results for empty microcapsules corresponding to sample #93

| No. | Subject | Sex | Age | 20 min after removal of 10$^{th}$ application | 24 hrs after removal of 10$^{th}$ application | 48 hrs after removal of 10$^{th}$ application |
|---|---|---|---|---|---|---|
| 1 | B. Y | F | 49 | 0 | 0 | 0 |
| 2 | H. M | M | 59 | 0 | 0 | 0 |
| 3 | G. A | F | 53 | 0 | 0 | 0 |
| 4 | G. G | M | 32 | 0 | 0 | 0 |
| 5 | G. M | M | 35 | 0 | 0 | 0 |
| 6 | G. D | F | 19 | 0 | 0 | 0 |
| 7 | H. A | F | 55 | 0 | 0 | 0 |
| 8 | C. R | F | 38 | 0 | 0 | 0 |
| 9 | C. G | M | 38 | 0 | 0 | 0 |
| 10 | H. E | F | 58 | 0 | 0 | 0 |
| 11 | C. M | M | 57 | 0 | 0 | 0 |
| 12 | S. S | F | 60 | 0 | 0 | 0 |
| 13 | P. S | F | 60 | 0 | 0 | 0 |
| 14 | P. S | M | 62 | 0 | 0 | 0 |
| 15 | P. V | F | 53 | 0 | 0 | 0 |
| 16 | O. S | F | 30 | 0 | 0 | 0 |
| 17 | O. L | F | 32 | 0 | 0 | 0 |
| 18 | E. H | F | 34 | 0 | 0 | 0 |
| 19 | S. G | F | 31 | 0 | 0 | 0 |
| 20 | R. A | M | 33 | 0 | 0 | 0 |
| 21 | Y. H | M | 35 | 0 | 0 | 0 |
| 22 | Y. L | F | 54 | 0 | 0 | 0 |
| 23 | S. G | F | 45 | 0 | 0 | 0 |
| 24 | I. G | M | 50 | 0 | 0 | 0 |
| 25 | G. C | F | 32 | 0 | 0 | 0 |
| 26 | B. B | F | 38 | 0 | 0 | 0 |
| 27 | G. G | M | 26 | 0 | 0 | 0 |
| 28 | A. U | M | 35 | 0 | 0 | 0 |
| 29 | M. H | F | 37 | 0 | 0 | 0 |
| 30 | P. Z | F | 50 | 0 | 0 | 0 |
| 31 | P. N | M | 52 | 0 | 0 | 0 |
| 32 | S. O | M | 45 | 0 | 0 | 0 |
| 33 | A. M | F | 45 | 0 | 0 | 0 |
| 34 | R. A | F | 45 | 0 | 0 | 0 |
| 35 | R. T | F | 19 | 0 | 0 | 0 |
| 36 | M. O | F | 50 | 0 | 0 | 0 |
| 37 | B. S | F | 50 | 0 | 0 | 0 |
| 38 | A. H | F | 40 | 0 | 0 | 0 |
| 39 | G. A | F | 49 | 0 | 0 | 0 |
| 40 | S. S | F | 19 | 0 | 0 | 0 |
| 41 | S. T | M | 28 | 0 | 0 | 0 |
| 42 | S. I | M | 26 | 0 | 0 | 0 |
| 43 | T. S | F | 22 | 0 | 0 | 0 |
| 44 | S. R | M | 58 | 0 | 0 | 0 |
| 45 | S. M | F | 27 | 0 | 0 | 0 |
| 46 | M. N | F | 42 | 0 | 0 | 0 |
| 47 | T. T | F | 40 | 0 | 0 | 0 |
| 48 | L. M | F | 29 | 0 | 0 | 0 |
| 49 | R. V | F | 43 | 0 | 0 | 0 |
| 50 | E. D | F | 33 | 0 | 0 | 0 |

Example 16. Microencapsulation of Chromium Oxide Green

Microencapsulated chromium oxide green was prepared by the following laboratory procedure:

16.1 Production of Chromium Oxide Green Inner Particles:

Syncrowax HRC (Tribehenin, 1200 gr) was heated until melted and chromium oxide green (800 gr) was gradually added under steering at 80-100° C. until a homogeneous dispersion was received (composition detailed in Table 13). The hot melt was then poured on an aluminum foil to receive a uniform thin layer of 2-3 mm, and allowed to cool and harden. The hard melt was then cut to slices of 1-1.5 cm. The melt was grounded using Rotor Beater Mill SR 300 (Retsch GmbH, Germany) to receive 15% 0-50 μm particles and 58% 50-100 μm particles. The inner particles were then mixed with Aerosil 200 (0.8% from total weight). The particles were stored in a closed container in the refrigerator, to prevent agglomeration at room temperature.

TABLE 13

Inner particles content

| | Materials | Loading on dry product (%) | Loading for 2 kg |
|---|---|---|---|
| 1 | Chromium Oxide Green | 60 | 1200 |
| 2 | Syncrowax HRC (Tribehenin) | 40 | 800 |

16.2 Preparation of Master Batch Containing Chromium Oxide Green Inner Particles:

EuRSPO (75 g) and ethyl cellulose (15 g) were gradually added to 1000 ml ethyl acetate under stirring at room temperature for 10 min until receiving clear solution. Titanium dioxide (45 g) was gradually added to the solution and stirred for 5 min. Boron nitride (15 g) was gradually added under stirring to the mixture and stirred for 5 min. The mixture was then transferred to a homogenizer (Dispermat® CL 54) and homogenized for 7 min until a homogeneous mixture was received. The green inner particles (obtained in 16.1 above) were then gradually added to the mixture under stirring and stirred for another 7 min (composition detailed in Table 14).

TABLE 14

Master Batch content

| # | Materials | Loading for 100 g dry product (%) | Loading components of pigment suspension (g) |
|---|---|---|---|
| 1 | EuRSPO | 25 | 75 |
| 2 | Ethyl Cellulose No7 | 5 | 15 |
| 3 | TiO2 | 15 | 45 |
| 4 | BN | 5 | 15 |
| 5 | Green Inner particles | 50 | 150 |
| 6 | Ethyl Acetate | | 900 |

EuRSPO—Eudragit RSPO ®

16.3 Preparation of the Emulsion:

A water solution was prepared by mixing water (4283.4 g) with polyvinyl alcohol (PVA 4%, 132.6 g) such that the water phase consisted of 0.12% PVA. Ethyl acetate (384 g) was added to water phase under stirring at 400 RPM for 10 min. The master batch (pigment suspension, prepared in 16.2 above) was gradually added into the ethyl acetate/water emulsion under stirring at 400 RPM, and further stirred for additional 10 min (composition detailed in Table 15). Ratio MB/Emulsion (w/w)=1/4; Temperature ≤16° C.

TABLE 15

| Emulsion content | |
|---|---|
| Materials | Loading for 300 g portion (g) |
| Pigment suspension | 1200 |
| Water solution reagents | |
| Water | 4283.4 |
| PVA solution 4% (0.12% from water phase) | 132.6 |
| Ethyl Acetate (10% from total Emulsion weight) | 384 |

16.4 Procedure of Extraction:

The extraction phase consisted of 26400 g water (see Table 16). The emulsion of 16.3 above (including the Master Batch and water solution) was gradually added into the extraction phase using manual pump, under very good stirring at 150 RPM, and was further stirred for additional 20 min. The extraction mixture was then left for overnight sedimentation of the formed microcapsules (temperature 20-23° C.).

TABLE 16

| Extraction content | |
|---|---|
| Materials | Loading for 300 g portion (g) |
| Master Batch | 1200 |
| Water solution | 4800 |
| Extraction fluid | |
| Water | 26400 |

16.5 Washing and Drying Procedure:

The sedimented microcapsules of 16.4 above were separated by filtration as a "cake". Water (2 L) was added to the filtrated "cake" (ratio weight of dry product/Water (w/w)—at least 1/7) and stirred for 10 min followed by filtration. This step of washing and filtering was repeated twice. The "cake" of microcapsules was then put into a container and crumbled with spatula (wet cake content about 20% of capsules and 80% water). The container with the wet capsules was placed in a freeze drying oven (Cham) and the microcapsules were freeze dried for 48 hours at −38° C. and 0.1-0.4 mBar. The dry capsules were mixed with Aerosil 200 colloidal silica (0.8% from total weight) and sifted with an automatic sifter (Ari j-Levy). The sifted microcapsules containing chromium oxide green were then refrigerated.

Figure 23:
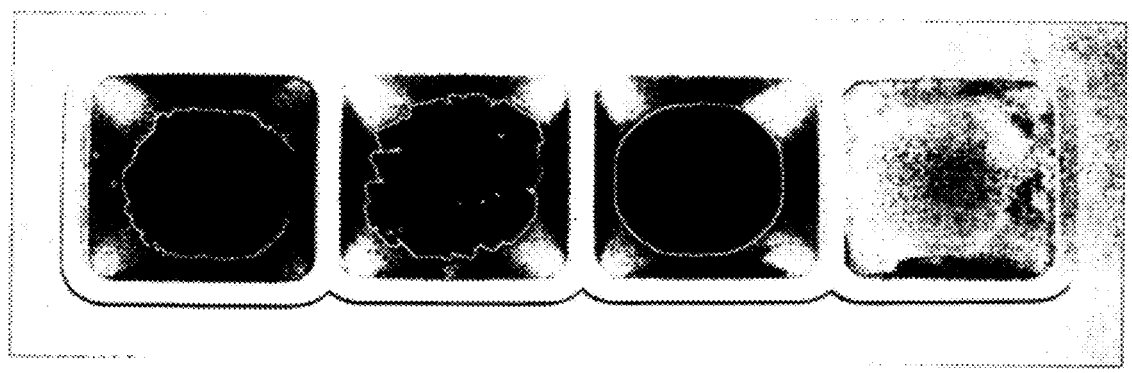
FIG. 23 illustrates various stages of chromium oxide green pigment processing up to the formation of microcapsules: (1) irregular aggregates of chromium oxide green particles (raw material); (2) irregular aggregates of hot-melt pigment particles with tribehenin following cooling; (3) fine grinding of wax encapsulated pigment particles; (4) second layer coating of (3).

The mean particle size of the green pigment microcapsules obtained was about 70 μm. FIG. 23 shows the green aggregates of chromium oxide green particles (raw material) vs. encapsulated pigment particles which are white (due to the $TiO_2$). Immediate release of the green pigment was obtained upon spreading when the shell fractured.

The invention claimed is:

1. Stable microcapsules for topical application comprising 0.1-99% benzoyl peroxide and a non-porous shell of a wall-forming polymeric material selected from the group consisting of a polyacrylate, a polymethacrylate, a cellulose ether, a cellulose ester, and a combination thereof, wherein at least a part of said benzoyl peroxide is in a core of said microcapsules and wherein said microcapsules immediately release the core-encapsulated benzoyl peroxide following contact with the skin.

2. The stable microcapsules of claim 1, wherein the benzoyl peroxide is released from said microcapsules by rubbing on the skin.

3. The stable microcapsules of claim 1, wherein said microcapsules have a mean particle size within a range selected from the group consisting of about 1 to about 500 μm, 10 to 130 μm, 10 to 100 μm, 20 to 90 μm, 30 to 70 μm, and 40 to 60 μm.

4. The stable microcapsules of claim 3, wherein said microcapsules have a mean particle size under 100 μm.

5. The stable microcapsules of claim 1, wherein each microcapsule comprises 20-99%, or 40-95% benzoyl peroxide.

6. The stable microcapsules of claim 1, wherein said wall-forming material is poly(methyl methacrylate) co-methacrylic acid, ammonio methacrylate copolymer type B, cellulose ethyl ether, cellulose ethyl ester, or a combination thereof.

7. The stable microcapsules of claim 6, wherein said wall-forming material is poly(methyl methacrylate) co-methacrylic acid or ethyl cellulose, optionally in combination with ammonio methacrylate copolymer type B.

8. The stable microcapsules of claim 1, further comprising one or more additives selected from the group consisting of one or more plasticizers, a wax, and boron nitride.

9. The stable microcapsules of claim 8, wherein the additive is one or more plasticizers selected from the group consisting of tricaprylin (TC), trilaurin (TL), acetyl tributyl citrate (ATBC), acetyl triethyl citrate (ATEC), triethyl citrate (TEC), C12-C15 alkyl benzoate (AB), isopropyl myristate, monoglycerol oleate, tripalmitin, triacetin, and paraffin oil; a wax selected from the group consisting of beeswax, abil wax, lanolin, triisostearin, isostearyl isostearate, stearic acid, cetyl alcohol, palmitic acid, glyceryl stearate, and propylene glycol mono palmitostearate; or a combination thereof.

10. The stable microcapsules of claim 6, wherein the wall-forming material is ethyl cellulose or poly(methyl methacrylate) co-methacrylic acid, further comprising the plasticizer trilaurin (TL), optionally in combination with the wax isostearyl isostearate, or the wax propylene glycol mono palmitostearate.

11. The stable microcapsules of claim 6, wherein the wall-forming material is ethyl cellulose, further comprising a combination of plasticizer/wax selected from the group consisting of trilaurin/beeswax, trilaurin/lanolin, trilaurin/triisostearin, trilaurin/isostearyl isostearate, trilaurin/abil wax, trilaurin/stearic acid, trilaurin/cetyl alcohol, trilaurin/palmitic acid, trilaurin/propylene glycol mono palmitostearate and trilaurin/glyceryl stearate.

12. A method for the preparation of microcapsules according to claim 1, comprising:
  a) preparing an organic solution of benzoyl peroxide with the wall-forming polymeric material in ethyl acetate, optionally in the presence of one or more additives;
  b) mixing said organic solution with an aqueous solution containing an emulsifier, under stirring, to form an emulsion;
  c) adding to the emulsion formed in (b) an excess amount of water containing the same emulsifier as in (b) to initiate extraction of the organic solvent from the emulsion, thus obtaining microcapsules;
  d) optionally allowing sedimentation of the microcapsules; and e) isolating said microcapsules of c) or d) by filtration, subsequently washing with water or with 10% alcohol, and optionally drying the wet capsules.

13. The method of claim 12, wherein said wall forming material is poly(methyl methacrylate) co-methacrylic acid, ammonio methacrylate copolymer type B, a cellulose ethyl ether, a cellulose ethyl ester, or a combination thereof.

14. The method of claim 12, wherein said additive is a plasticizer selected from the group consisting of tricaprylin (TC), trilaurin (TL), acetyl tributyl citrate (ATBC), acetyl triethyl citrate (ATEC), triethyl citrate (TEC), C12-C15 alkyl benzoate (AB), isopropyl myristate, monoglycerol oleate, tripalmitin, triacetin, paraffin oil, and a combination thereof; a wax selected from the group consisting of beeswax, abil wax, lanoline, triisostearin, isostearyl isostearate, stearic acid, cetyl alcohol, palmitic acid, propylene glycol mono palmitostearate, and glyceryl stearate; a non-waxy fatty acid; boron nitride (BN); or a combination thereof.

15. A composition for topical application comprising benzoyl peroxide microcapsules according to claim 1.

16. The composition of claim 15, wherein the final concentration of benzoyl peroxide in the composition is in the range of 0.1-10%.

17. The composition of claim 15, further comprising one or more active agents selected from the group consisting of antibiotics and vitamin A or a derivative thereof, optionally microencapsulated in separate microcapsules.

18. The composition of claim 17, wherein the antibiotic is clarithromycin, erythromycin, clindamycin or azithromycin, and the vitamin A or derivative thereof is retinol, retinal, retinoic acid or retinol ester.

19. The composition of claim 15, further comprising a green dye, optionally microencapsulated in a shell of a wall-forming polymeric material selected from the group consisting of a polyacrylate, a polymethacrylate, a cellulose ether, a cellulose ester, and a combination thereof.

20. The composition of claim 19, wherein the green dye is chromium oxide green pigment and the wall-forming polymeric material is a combination of ethyl cellulose and ammonio methacrylate copolymer type B, optionally further comprising a white pigment, and further additives including boron nitride.

21. The composition of claim 15, in the form of cream, ointment, paste, lotion intended for skin care, or gel.

22. The composition of claim 15, for the treatment of acne.

23. The stable microcapsules of claim 4, wherein said microcapsules have a mean particle size under 30 to 70 μm.

24. The stable microcapsules of claim 5, wherein each microcapsule comprises 60-90% benzoyl peroxide.

25. The composition of claim 16, wherein the final concentration of benzoyl peroxide in the composition is in the range of 1-5%.

26. The composition of claim 20, wherein said white pigment is $TiO_2$.

27. The composition of claim 21, wherein said gel is a water-based gel.

28. The stable microcapsules of claim 1, wherein a part of the benzoyl peroxide is also found in said shell, solubilized in the polymeric material.

\* \* \* \* \*